(12) United States Patent
Zhao et al.

(10) Patent No.: US 11,947,259 B2
(45) Date of Patent: *Apr. 2, 2024

(54) PHOTOINITIATOR COMPOSITION CONTAINING ACYLCARBAZOLE DERIVATIVE AND CARBAZOLYL OXIME ESTER, AND USE THEREOF IN PHOTOCURABLE COMPOSITION

(71) Applicant: IGM (ANQING) HIGH TECHNOLOGY DEVELOPMENT CO., LTD, Anhui (CN)

(72) Inventors: Wenchao Zhao, Nantong (CN); Chenlong Wang, Nantong (CN); Jiaqi Li, Nantong (CN); Yonglin Wang, Nantong (CN)

(73) Assignee: IGM (ANQING) HIGH TECHNOLOGY DEVELOPMENT CO., LTD, Anhui (CN)

( * ) Notice: Subject to any disclaimer, the term of this patent is extended or adjusted under 35 U.S.C. 154(b) by 119 days.

This patent is subject to a terminal disclaimer.

(21) Appl. No.: 17/598,434

(22) PCT Filed: Mar. 17, 2020

(86) PCT No.: PCT/CN2020/079715
§ 371 (c)(1),
(2) Date: Sep. 27, 2021

(87) PCT Pub. No.: WO2020/253284
PCT Pub. Date: Dec. 24, 2020

(65) Prior Publication Data
US 2022/0179309 A1    Jun. 9, 2022

(30) Foreign Application Priority Data

Jun. 21, 2019 (CN) .......................... 201910540498.3

(51) Int. Cl.
| | | |
|---|---|---|
| C08F 2/46 | (2006.01) | |
| C07D 209/88 | (2006.01) | |
| C08F 2/48 | (2006.01) | |
| C08F 2/50 | (2006.01) | |
| C08G 61/04 | (2006.01) | |
| G03F 7/027 | (2006.01) | |

(52) U.S. Cl.
CPC ........... *G03F 7/027* (2013.01); *C07D 209/88* (2013.01); *C08F 2/48* (2013.01)

(58) Field of Classification Search
CPC .... C08F 2/50; C08F 2/48; G03F 7/031; G03F 7/105; G03F 7/007; G03F 7/027; G02B 5/20; C07D 209/88; C07D 209/82
USPC .............. 522/167, 1, 6, 189, 184, 71; 520/1
See application file for complete search history.

(56) References Cited

U.S. PATENT DOCUMENTS

| | | |
|---|---|---|
| 2004/0170924 A1 | 9/2004 | Kunimoto et al. |
| 2011/0121435 A1 | 5/2011 | Mitsukura et al. |
| 2013/0188270 A1 | 7/2013 | Nishimae et al. |
| 2014/0220491 A1 | 8/2014 | Cho et al. |
| 2017/0283520 A1 | 10/2017 | Sawamoto et al. |
| 2020/3071435 | 11/2020 | Terakawa |
| 2022/0185775 A1* | 6/2022 | Zhao .................... C07D 209/56 |

FOREIGN PATENT DOCUMENTS

| | | |
|---|---|---|
| CN | 1922142 A | 2/2007 |
| CN | 100528838 C | 8/2009 |
| CN | 101528693 A | 9/2009 |
| CN | 101528694 A | 9/2009 |
| CN | 101910350 A | 12/2010 |
| CN | 101941939 A | 1/2011 |
| CN | 103153952 A | 6/2013 |
| CN | 103492948 A | 1/2014 |
| CN | 107793502 A | 3/2018 |
| EP | 2407456 A1 | 1/2012 |
| IN | 101508744 A | 8/2009 |
| JP | 2007112930 | 5/2007 |
| JP | 2007219362 | 8/2007 |
| JP | 2007277512 A | 10/2007 |
| JP | 2012194516 A | 10/2012 |
| JP | 2019091034 A | 6/2019 |
| KR | 1020140032938 A | 3/2014 |
| WO | 2008075564 A1 | 6/2008 |
| WO | 2012068879 A1 | 5/2012 |

OTHER PUBLICATIONS

1st Office Action in corresponding JP Application Published as JP2022538451 published Jun. 10, 2022 (4 pg) and English translation (2 pg).
Office Action from Corresp0nding Taiwanese Application, Application No. 109109043; Ser. No. 11020505940; dated May 28, 2021.
International Search Report from PCT/CN2020/079715, the international phase of this the present application, the ISR dated Jun. 30, 2020 (2 pages).
Written Opinion of the International Search Authority in PCT/CN2020/079715, the international phase ofthe present application, 4 pages.
2nd Office Action dated Apr. 5, 2023 in corresponding JP Application Published as JP2022538451 published Jun. 10, 2022 (2 pg) and English translation (1 pg).
English Translation of First Office Action dated Oct. 27, 2023 in Corresponding Chinese Patent Application CN 20208001288.5 (4 pages).

(Continued)

*Primary Examiner* — Jessica Whiteley
(74) *Attorney, Agent, or Firm* — Irving M. Fishman

(57) ABSTRACT

Provided is a photoinitiator composition containing an acylcarbazole derivative and a carbazolyl oxime ester. The photoinitiator composition is used in a photocurable composition, especially a photoresist formulation, and exhibits the best sensibilization effect when the molar ratio of the acylcarbazole derivative to the carbazolyl oxime ester photoinitiator is between 0.1 and 1.4.

19 Claims, No Drawings

(56) References Cited

OTHER PUBLICATIONS

English translation of Office Action of Oct. 9, 2023 in Corresponding German Patent Application DE 11 2020 002 200.5 (3 pages).
English Translation of Office Action dated Jan. 4, 2024 in Corresponding Korean Patent Application KR10-2021-7039312 (9 pages).

* cited by examiner

PHOTOINITIATOR COMPOSITION CONTAINING ACYLCARBAZOLE DERIVATIVE AND CARBAZOLYL OXIME ESTER, AND USE THEREOF IN PHOTOCURABLE COMPOSITION

TECHNICAL FIELD

The present invention belongs to the technical field of photocuring technique, and particularly relates to a photoinitiator composition comprising a high-activity sensitizing agent and a carbazolyl oxime ester and use thereof in a photocurable composition, especially in the manufacturing of a photoresist.

BACKGROUND

Photocuring technique has been widely used since 1970s. For example, UV photocuring technique is widely used in the fields of coatings, printing inks and electronic device manufacturing. Photoinitiators and co-initiators such as sensitizing agents are key factors affecting curing efficiency. Carbazolyl oxime ester is an important class of oxime ester photoinitiators, and is well known, studied and used by those skilled in the art due to its relatively high sensitivity. For example, carbazolyl oxime ester compounds with various substituents and their use in materials or devices such as color filters, black matrixes, optical spacers and liquid crystal segmentation orientation were disclosed in CN1922142A (Mitsubishi Chemical), CN100528838C (02), CN101528694A (831), CN101528693A, CN101508744A (304), CN103153952A (03), CN103492948A and, CN107793502A. In order to improve the color saturation or hiding power, the content of pigment in the photocurable formula is getting higher and higher, especially in black photoresists, while the light energy utilization rate in the curing process is reduced due to the absorption by pigment. Therefore, it is necessary to develop a photoinitiator or a photoinitiator composition with higher sensitivity. Further, sensitizing the existing photoinitiators is also one of the methods to improve the sensitivity. Sensitizing agents described in the prior art such as CN100528838C includes benzophenone and derivatives thereof, thioxanthone and derivatives thereof, anthraquinone and derivatives thereof, coumarin derivatives, camphorquinone, phenothiazine and derivatives thereof, 3-(aroylmethylene) thiazolines, rhodanine and derivatives thereof, eosine, rhodamine, acridine, anthocyanin, merocyanine dyes and tertiary amine compounds, wherein benzophenone and derivatives thereof, thioxanthone and derivatives thereof, anthraquinone and derivatives thereof, and coumarin derivatives are preferred.

Experiments show that these sensitizing agents do not show satisfactory sensitizing effect when mixing with carbazolyl oxime ester. Some compounds such as eosin, anthocyanin and phenothiazine even reduce the photocuring efficiency of photocurable composition formula due to the presence of phenolic hydroxyls or anilino groups. As for the four preferred kinds of compounds, although they are photoinitiators themselves, they have much lower photoinitiation efficiency than carbazolyl oxime ester compounds, and they do not show synergistic sensitizing effect when mixing with carbazolyl oxime ester. Therefore, there is actually no ideal sensitizing agent in the prior art.

However, there is an ever-growing need in the art to improve the performances such as exposure sensitivity, resolution, thermal stability, etc. The existing products and formula technologies are constantly facing new challenges.

SUMMARY OF THE INVENTION

The inventors have found that the acylcarbazole derivative of formula I shows a significant sensibilization effect when it is used together with a oxazolyl oxime ester at a specific ratio, and the sensibilization effects are significantly higher than that of those compounds disclosed in the prior art.

Therefore, in a first aspect, a photoinitiator composition comprising a sensitizing agent and a carbazolyl oxime ester is provided, wherein the sensitizing agent is selected from the group consisting of acylcarbazole derivatives of formula I, acyl benzocarbazole derivatives of formula II-A, II-B, or II-C, acyl dibenzocarbazole derivatives of formula II-D or II-E, and bicyclic carbazole derivatives of formula II-F, II-G or II-H, and wherein the carbazolyl oxime ester is selected from the group consisting of compounds of formulas III and IV-A to IV-E:

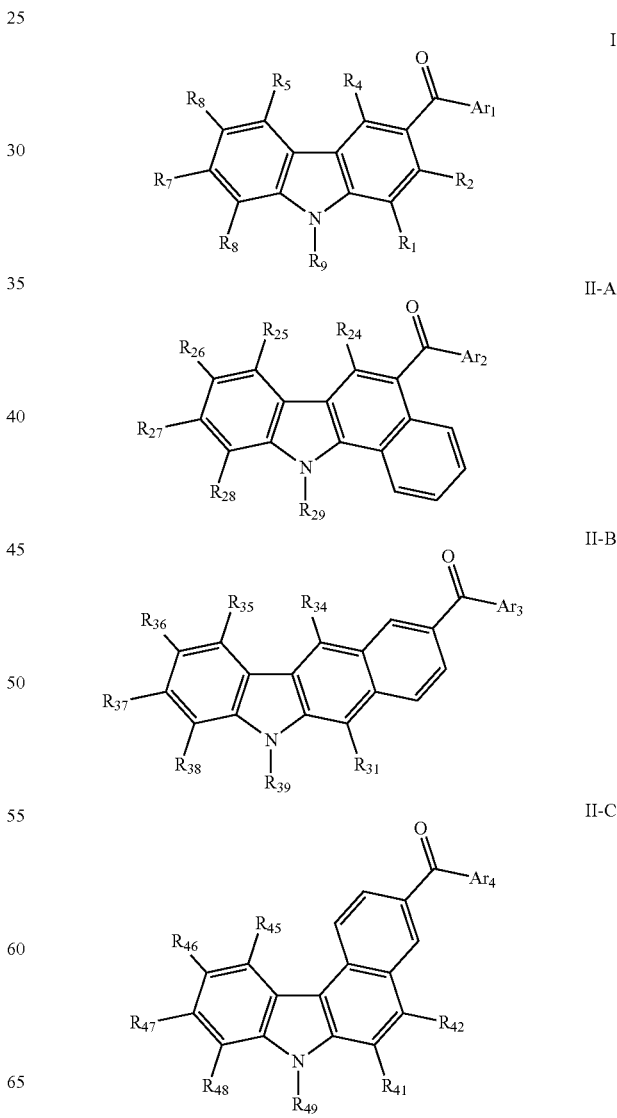

3
-continued

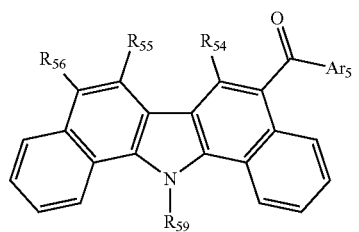
II-D

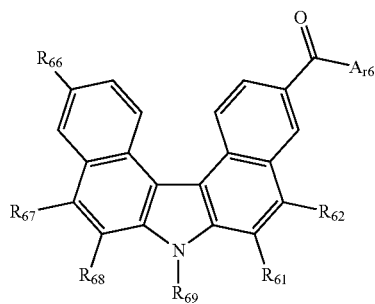
II-E

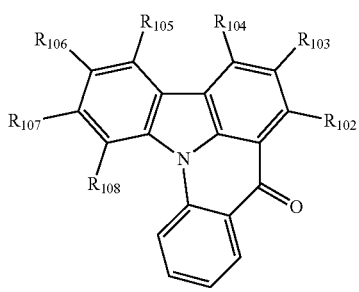
II-F

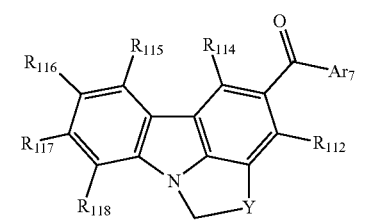
II-G

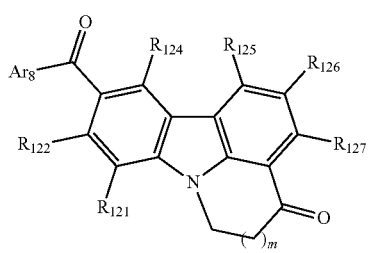
II-H

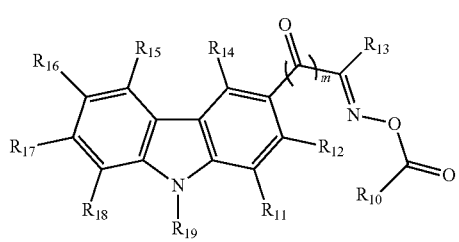
III

4
-continued

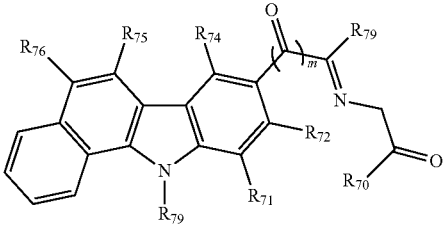
IV-A

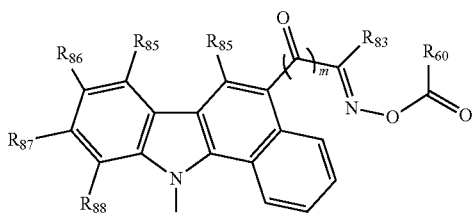
IV-B

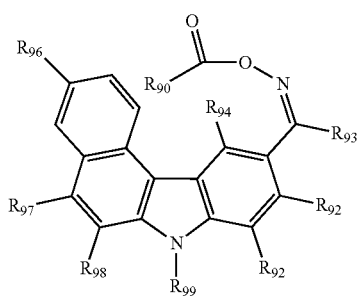
IV-C

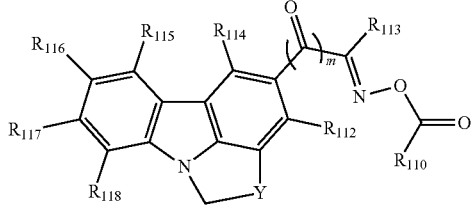
IV-D

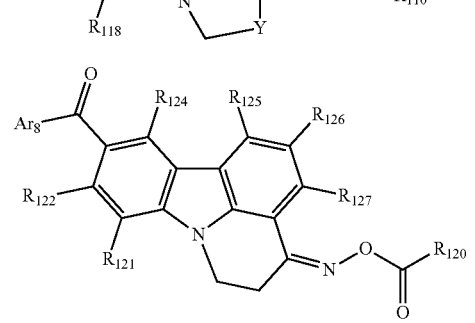
IV-E wherein, $R_1$, $R_2$, $R_4$, $R_5$, $R_7$, $R_8$, $R_{24}$, $R_{25}$, $R_{27}$, $R_{28}$, $R_{34}$, $R_{35}$, $R_{37}$, $R_{38}$, $R_{41}$, $R_{42}$, $R_{44}$, $R_{45}$, $R_{47}$, $R_{48}$, $R_{54}$, $R_{55}$, $R_{61}$, $R_{62}$, $R_{67}$, $R_{68}$, $R_{102}$-$R_{108}$, $R_{112}$, $R_{114}$, $R_{115}$, $R_{117}$, $R_{118}$, $R_{121}$, $R_{122}$ and $R_{124}$-$R_{127}$ are each independently selected from the group consisting of H, halogen, C1-C8 alkyl, C1-C8 alkoxy, and CN;

$R_{11}$, $R_{12}$, $R_{14}$, $R_{15}$, $R_{17}$, $R_{18}$, $R_{71}$, $R_{72}$, $R_{74}$, $R_{75}$, $R_{84}$, $R_{85}$, $R_{87}$, $R_{88}$, $R_{91}$, $R_{92}$, $R_{94}$, $R_{97}$ and $R_{98}$ are each independently selected from the group consisting of H, C1-C8 alkyl, C1-C8 alkoxy, halogen, CN and $NO_2$;

$R_6$, $R_{26}$, $R_{36}$, $R_{46}$, $R_{56}$, $R_{66}$, $R_{106}$ and $R_{116}$ each independently selected from the group consisting of H, halogen, CN, C1-C8 alkyl, C1-C12 alkyl acyl, C5-C6 substituted C1-C3 alkyl acyl, C6-C20 aroyl, C4-C20 heteroaryl acyl,

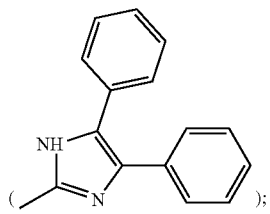 [SMILES: Cc1nc(-c2ccccc2)c(-c2ccccc2)[nH]1]

or wherein the above groups can optionally be connected with other adjacent substituents together with the parent structure to form a five-membered to seven-membered ring; wherein the C6-C20 aroyl and the C4-C20 heteroaryl acyl are independently substituted by substituents selected from the group consisting of H, halogen, $R_{40}$, $OR_{50}$, $SR_{50}$, $NR_{51}R_{52}$, $COOR_{50}$ and $CONR_{51}R_{52}$;

$R_9$, $R_{29}$, $R_{39}$, $R_{49}$, $R_{59}$, $R_{69}$, $R_{19}$, $R_{79}$, $R_{89}$ and $R_{99}$ are each independently selected from the group consisting of C1-C12 straight or branched alkyl, C2-C12 alkenyl, C3-C12 alkenyl alkyl, wherein hydrogen atoms on the carbon atoms being unsubstituted or substituted by one or more groups selected from the group consisting of: phenyl, C5-C6 cycloalkyl, C3-C6 heterocyclic group, halogen, $COOR_{20}$, $OR_{20}$, $SR_{20}$, $PO(OC_nH_{2n+1})_2$, and $Si(C_nH_{2n+1})_3$, wherein n is an integer from 1 to 4;

or $R_9$, $R_{29}$, $R_{39}$, $R_{49}$, $R_{59}$, $R_{69}$, $R_{19}$, $R_{79}$, $R_{89}$ and $R_{99}$ are each independently selected from the group consisting of C3-C12 alkyl and C3-C12 alkenyl alkyl, with its alkyl chain being interrupted by one or more groups selected from the group consisting of O, S, SO, $SO_2$, CO and COO;

or $R_9$, $R_{29}$, $R_{39}$, $R_{49}$, $R_{59}$, $R_{69}$, $R_{19}$, $R_{79}$, $R_{89}$ and $R_{99}$ are each independently selected from the group consisting of C2-C12 alkylene and double bond-containing C4-C12 alkylene, wherein groups connected with the terminal of the C2-C12 alkylene and the double bond-containing C4-C12 alkylene have the same definition as the groups originally connected with $R_9$, $R_{29}$, $R_{39}$, $R_{49}$, $R_{59}$, $R_{69}$, $R_{19}$, $R_{79}$, $R_{89}$ and $R_{99}$, that is, forming a symmetric or asymmetric N,N'-bicarbazole structure;

or $R_9$, $R_{29}$, $R_{39}$, $R_{49}$, $R_{59}$, $R_{69}$, $R_{19}$, $R_{79}$, $R_{89}$ and $R_{99}$ are each independently phenyl unsubstituted or substituted by one or more groups selected from the group consisting of: C1-C8 alkyl, halogen, $OR_{20}$, $SR_{20}$, $COR_{30}$, CN, COOH and

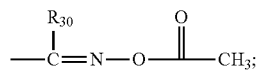

$R_{16}$, $R_{76}$, $R_{86}$, $R_{96}$, $R_{116}$ are each independently selected from the group consisting of C6-C20 aroyl, C4-C10 heteroaryl acyl, $NO_2$, 4,5-diphenylimidazol-2yl; and when $R_{16}$, $R_{76}$, $R_{86}$, $R_{96}$ and $R_{116}$ are each independently selected from the group consisting of C6-C20 aroyl or C4-C10 heteroaryl acyl, substituents at ortho-position of the acyl on the aromatic ring or heteroaromatic ring can be optionally connected with the carbazole ring;

$R_{13}$, $R_{73}$, $R_{83}$, $R_{93}$ and $R_{113}$ are each independently selected from the group consisting of C1-C8 alkyl, and C1-C3 alkyl substituted by C5-C6 cycloalkyl group or phenyl at terminal thereof, or the above-mentioned alkyl can optionally form a ring together with carbon or substituents on the carbon on an adjacent parent ring; provided that $R_{16}$, $R_{76}$, $R_{86}$, $R_{96}$ on the same molecule are each independently selected from C6-C20 aroyl or C4-C20 heteroaroyl group;

or $R_{13}$, $R_{73}$, $R_{83}$ and $R_{93}$ are each independently selected from the group consisting of C6-C20 aryl, C6-C20 aroyl, C4-C20 heteroaroyl, provided that $R_{16}$, $R_{76}$, $R_{86}$ and $R_{96}$ on the same molecule are each independently selected from the group consisting of C6-C20 aroyl, C4-C20 heteroaryl acyl, $NO_2$ and 4,5-diphenylimidazol-2-yl

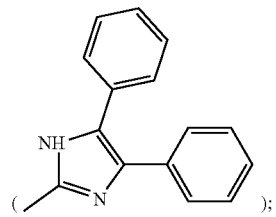 [SMILES: Cc1nc(-c2ccccc2)c(-c2ccccc2)[nH]1]

$R_{10}$, $R_{70}$, $R_{80}$, $R_{90}$, $R_{110}$, $R_{120}$ and $R_{130}$ are each independently selected from C1-C12 alkyl and C6-C20 aryl; wherein methyl or phenyl is preferred;

$Ar_1$, $Ar_2$, $Ar_3$, $Ar_4$, $Ar_5$, $Ar_6$, $Ar_7$ and $Ar_8$ are each independently selected from C6-C20 aroyl, C4-C20 heteroaroyl, wherein ortho-position of acyl on $Ar_1$, $Ar_2$ and $Ar_5$ can be optionally connected to a carbazole ring via O atom or S atom;

Y is straight or branched C1-C3 alkylene;

m=0 or 1;

substituents on all the above C6-C20 aryl and C4-C20 heteroaryl comprise H, halogen, CN, $R_{40}$, $OR_{50}$, $SR_{50}$, $NR_{51}R_{52}$, $COOR_{50}$ and $CONR_{51}R_{52}$, wherein halogen atoms are preferred; wherein the halogen is preferably fluorine;

$R_{20}$ and $R_{30}$ are each independently selected from the group consisting of H, C1-C8 alkyl, C1-C8 alkyl substituted by one or more groups selected from halogen and C5-C6 cycloalkyl, phenyl, phenyl substituted by one or more halogen, and C1-C4 alkyl acyl;

$R_{40}$ and $R_{50}$ are each independently selected from the group consisting of C1-C8 alkyl, C1-C8 alkyl substituted by one or more groups selected from F, Cl and hydroxyl, C3-C8 alkyl interrupted by one or more oxygen atoms and substituted by hydroxyl and acetoxy, a five-membered or six-membered ring containing one or two of heteroatoms selected from O, S and N, phenyl, C1-C4 alkylphenyl;

$R_{51}$ and $R_{52}$ are each independently selected from the group consisting of C1-C4 alkyl, and hydroxyl substituted C1-C4 alkyl;

or $NR_{51}R_{52}$ is a ring structure selected from the group consisting of

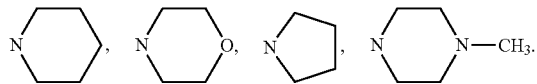

Preferably, aryl groups in the above mentioned C6-C20 aroyl are selected from the group consisting of phenyl, naphthyl, anthryl, and phenanthryl, etc., preferably phenyl, and the substituents thereof are selected from the group consisting of H, halogen, $R_{40}$, $OR_{50}$, $SR_{50}$, and $NR_{51}R_{52}$, etc. Substituents on the benzene ring are preferably in the 4-position, 2-position or 3,4-positions, 2,4-positions, 2,6-positions, 3,5-positions, 3,4,5-positions, or 2,4,6-positions.

Preferably, the heteroaryl in the above mentioned C4-C20 heteroarylacyl is selected from the group consisting of thienyl, benzo[b]thienyl, thianthrenyl, furyl, dibenzofuranyl, benzopyridyl, thioxanthyl, phenothiazinyl, pyrrolyl, imidazolyl, pyrazolyl, carbazolyl, pyrazinyl, pyrimidinyl, pyridazinyl, azaindenyl, indolyl, isoindolyl, quinolyl, isoquinolyl and naphthyridinyl, wherein thienyl is preferred.

Preferably, a molar ratio of the sensitizing agent to the carbazolyl oxime ester is 0.01:1 to 2:1, preferably 0.1:1 to 1.4:1, and more preferably 0.22:1 to 1.3:1.

Preferably, the sensitizing agent of formula I is selected from compounds of formulas I-1 to I-36 and any combination thereof:

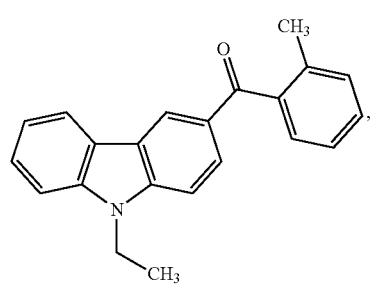
I-1

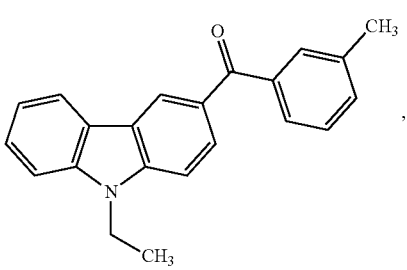
I-2

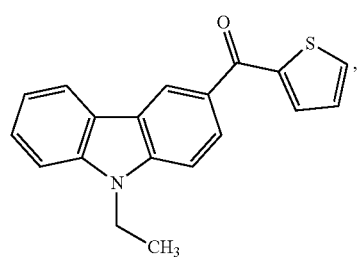
I-3

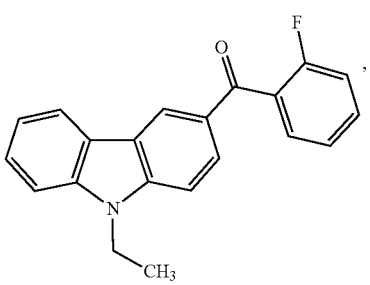
I-4

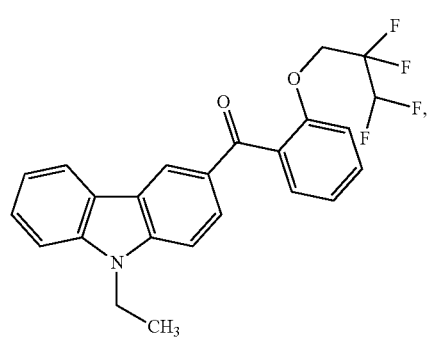
I-5

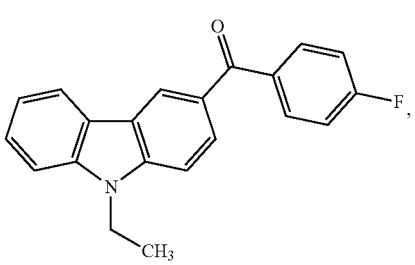
I-6

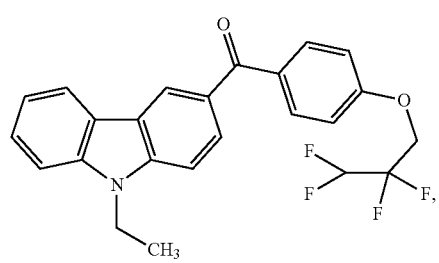
I-7

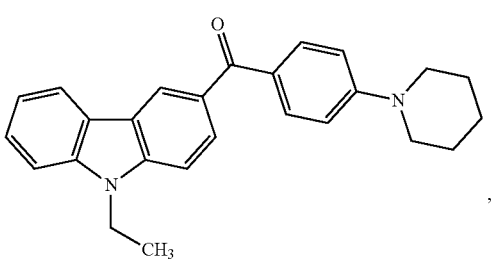
I-8

-continued
I-9
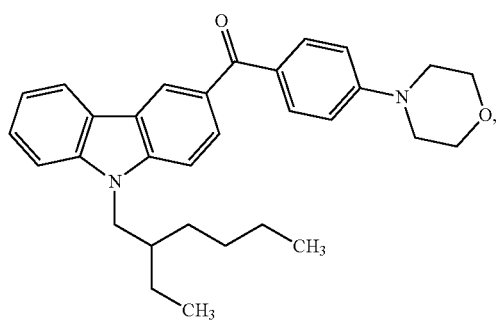
I-10
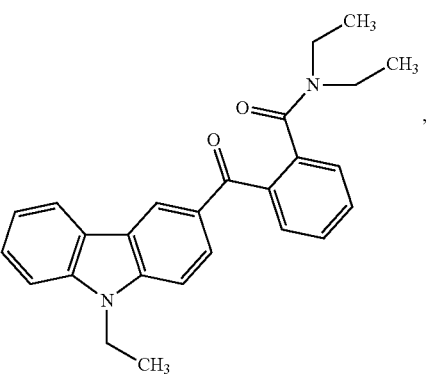
I-11
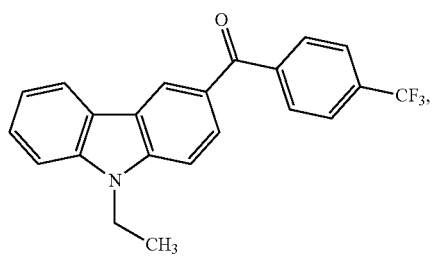
I-12
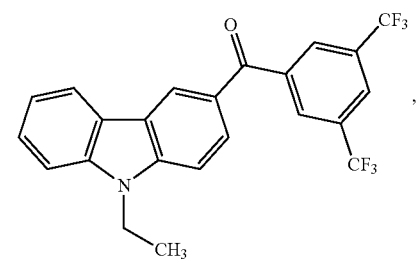
I-13
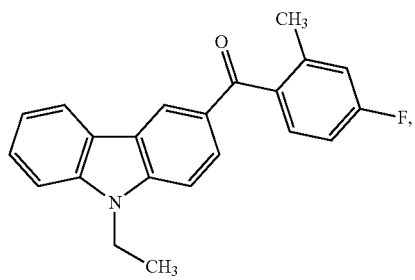
I-14
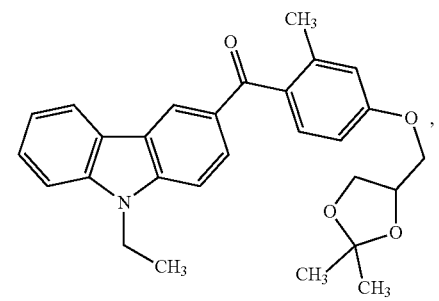
I-15
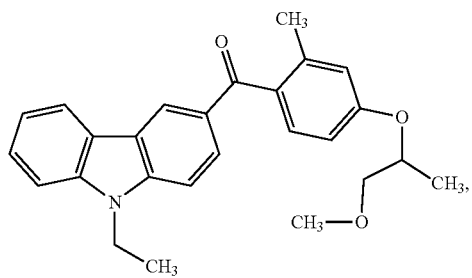
I-16
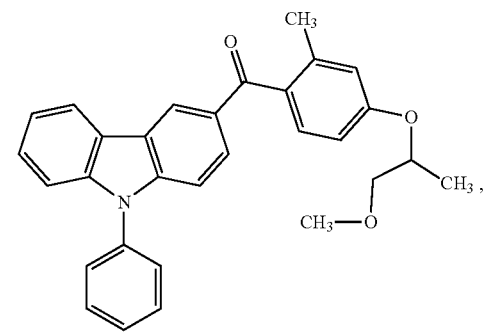
I-17
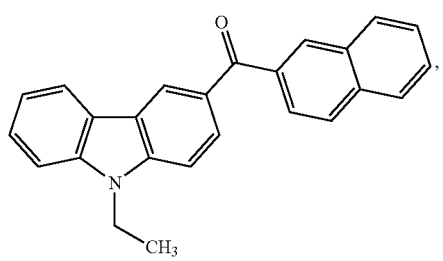
I-18
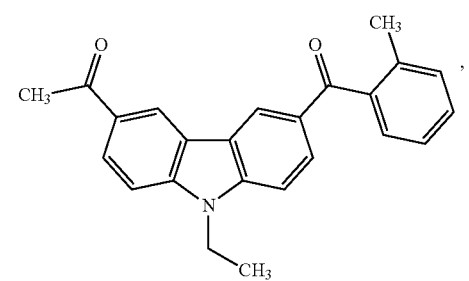

-continued
I-19
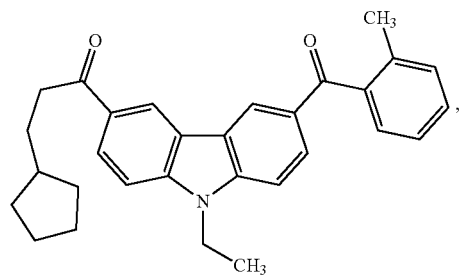
I-20
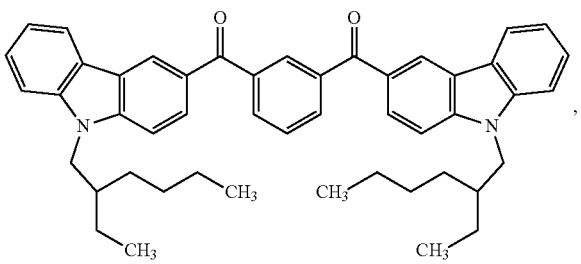
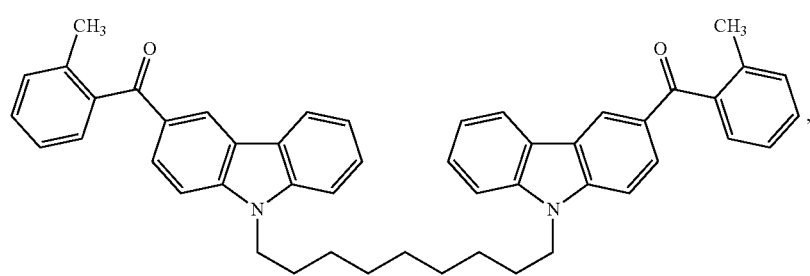
I-21
I-23
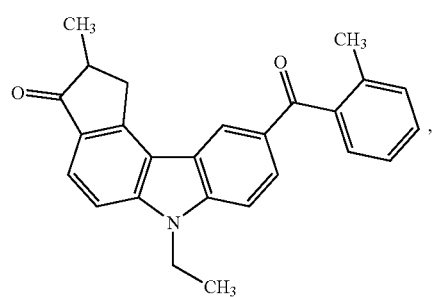
I-22
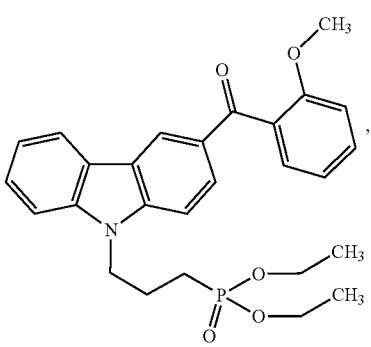
I-24
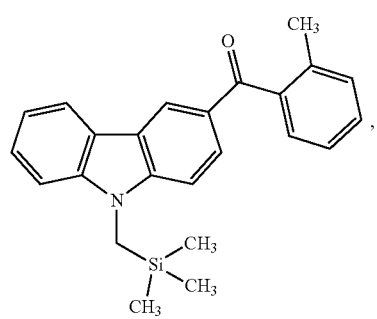
I-25
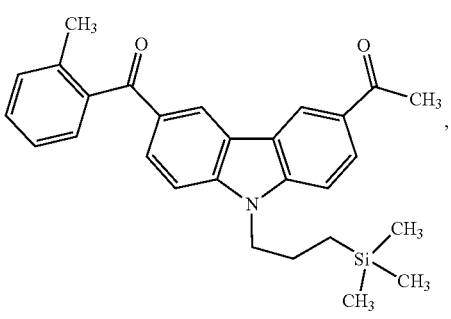
I-26
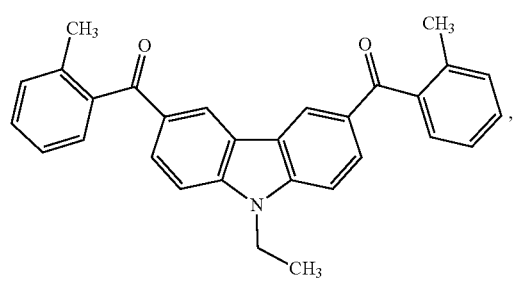
I-27
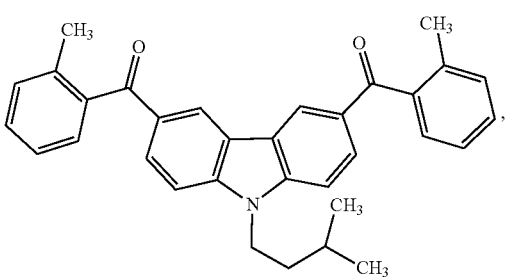

-continued
I-28
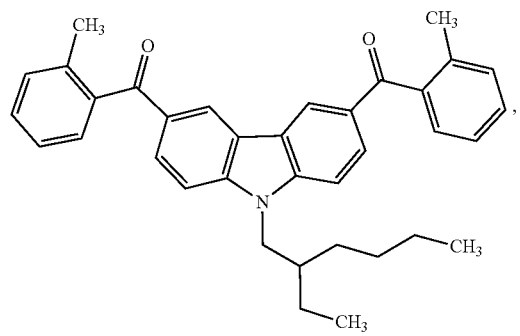
I-29
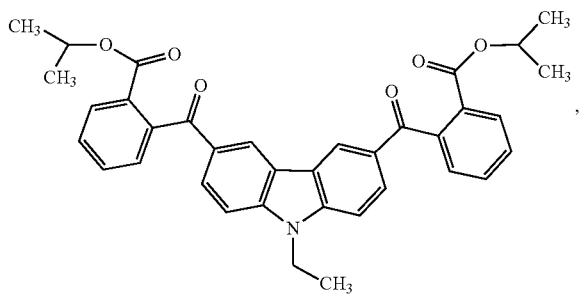
I-30
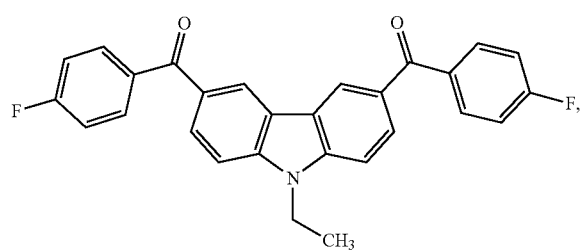
I-31
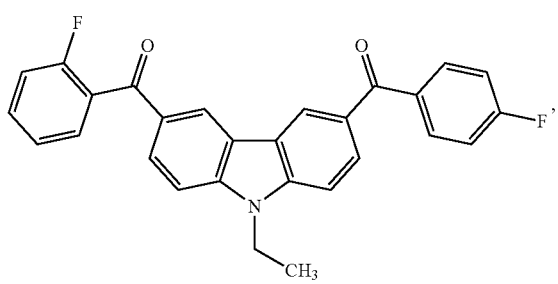
I-31
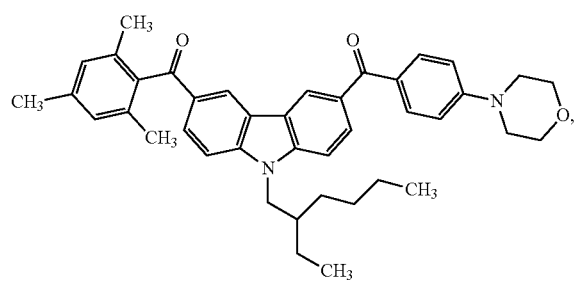
I-33
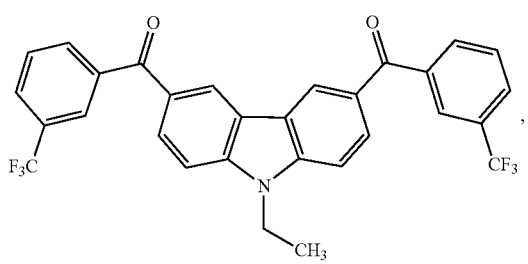
I-34
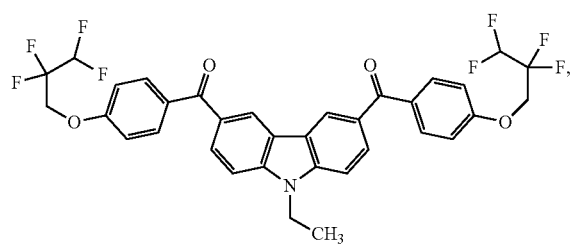
I-35
, and
I-36
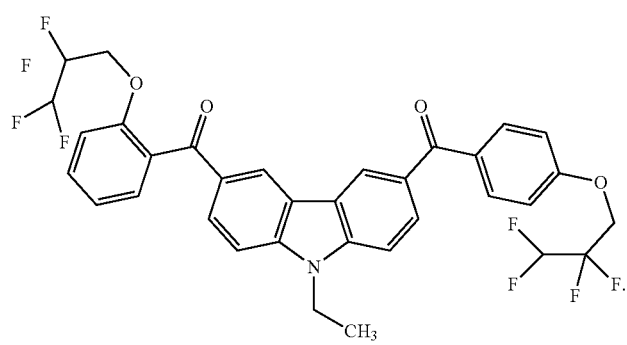

Preferably, the sensitizing agent of formulas II-A to II-H is selected from compounds of formulas II-1 to II-16 and any combination thereof:
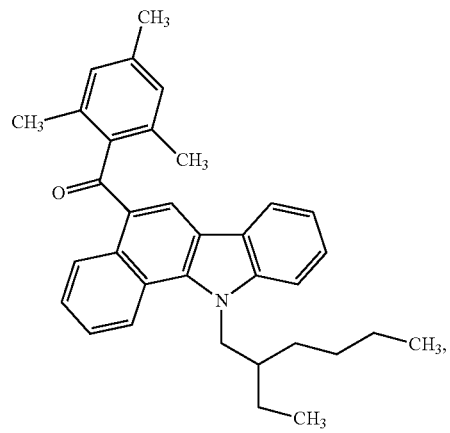
II-1
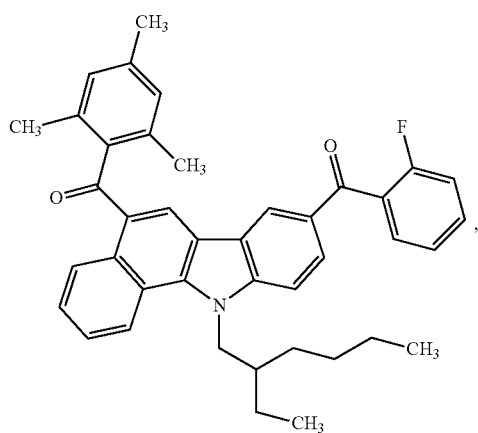
II-2
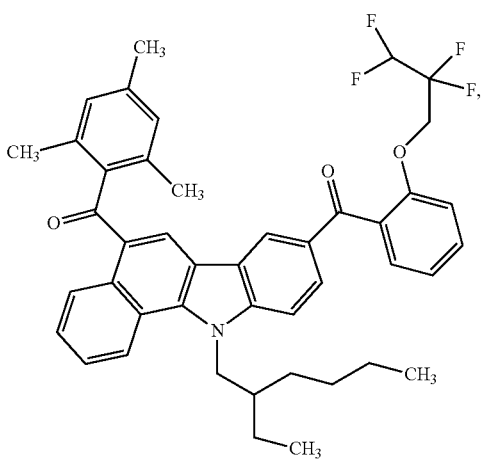
II-3
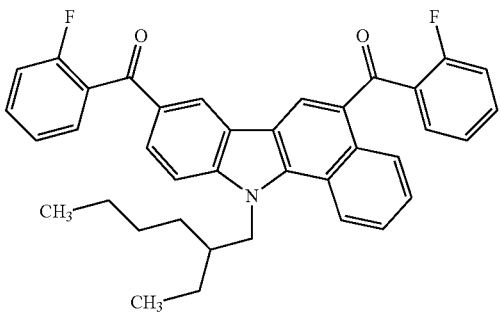
II-4
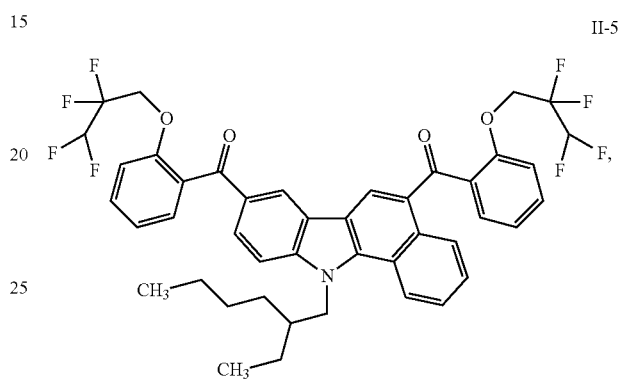
II-5
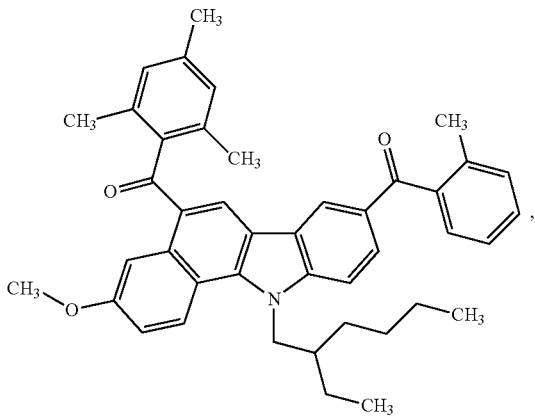
II-6
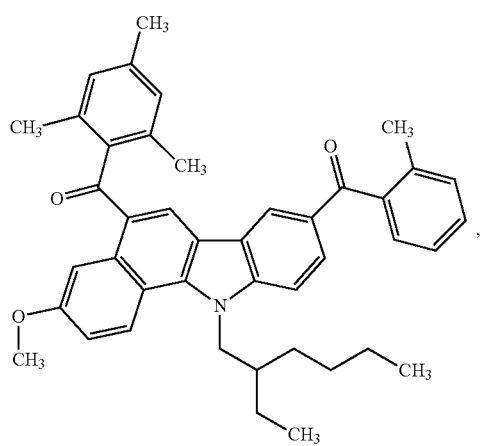
II-7

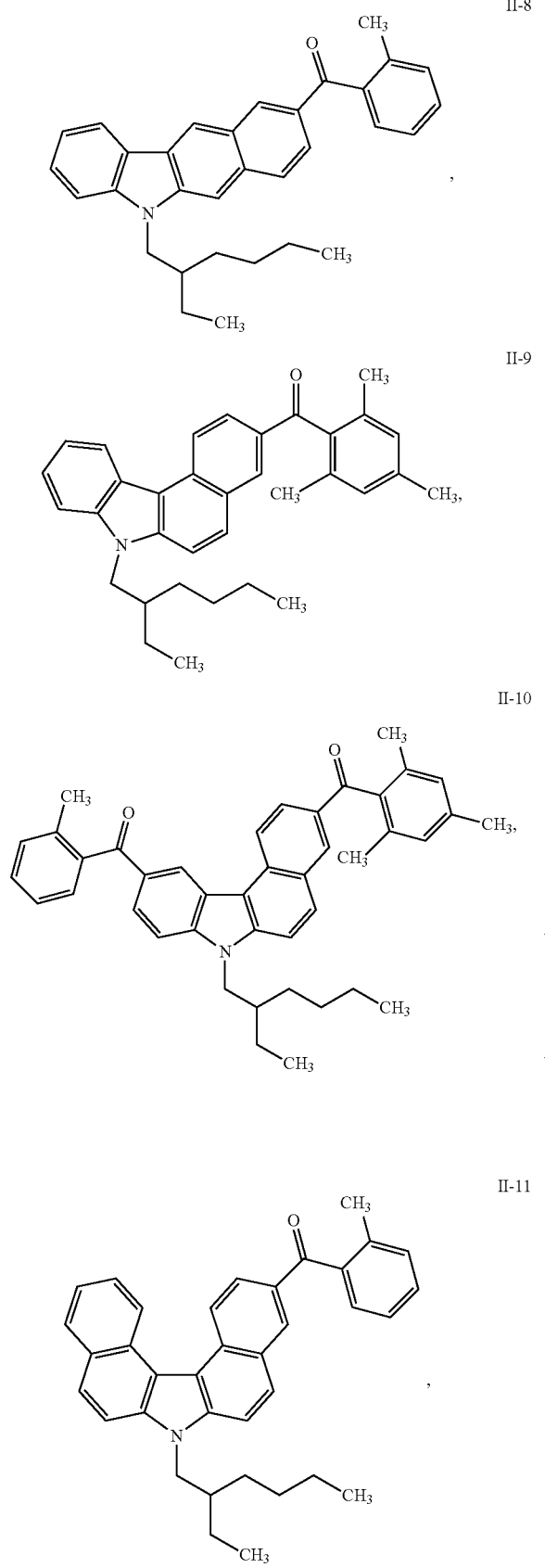
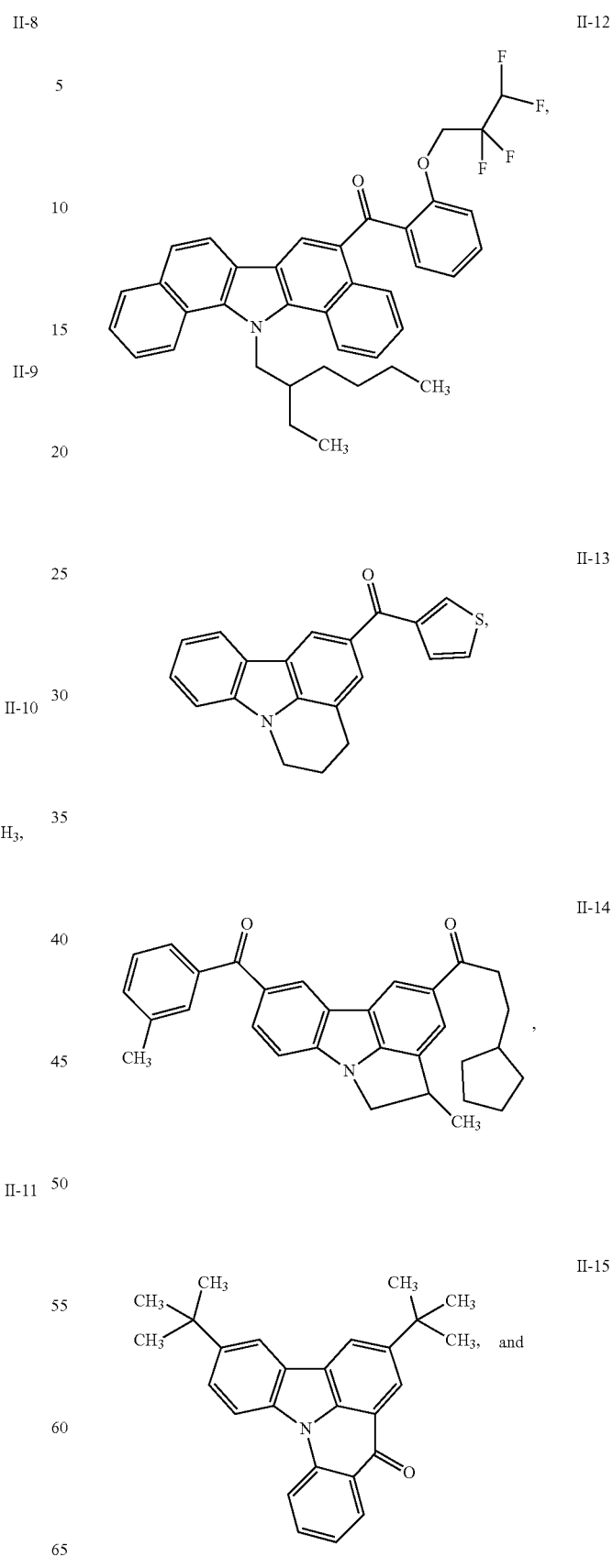

II-16
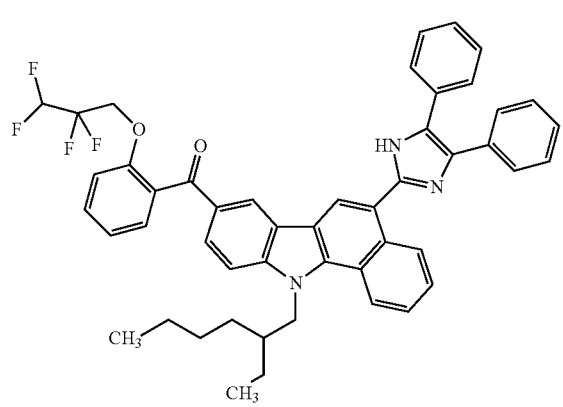
Preferably, the carbazolyl oxime ester of formula III is selected from compounds of formulas III-1 to III-17 and any combination thereof:
III-1
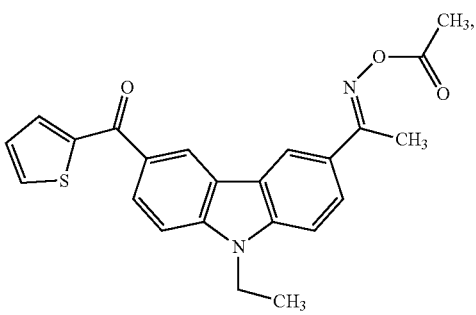
III-4
III-2
III-5
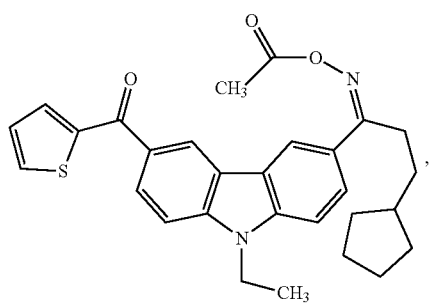
III-6
III-3
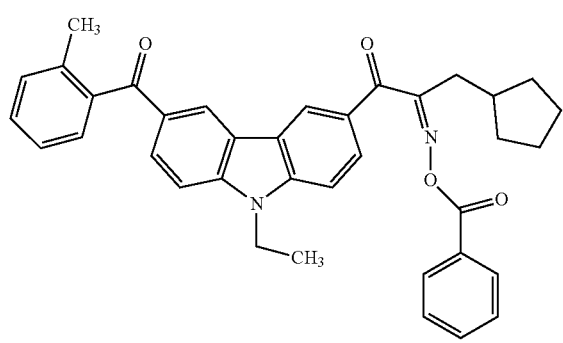
III-7
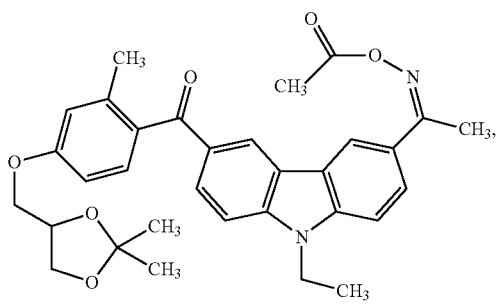
III-8
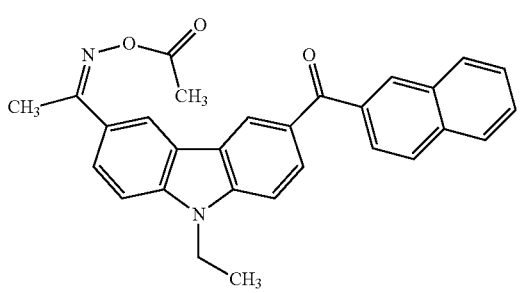
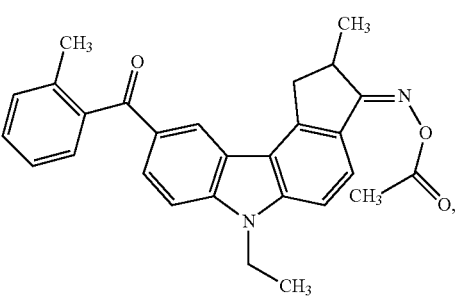

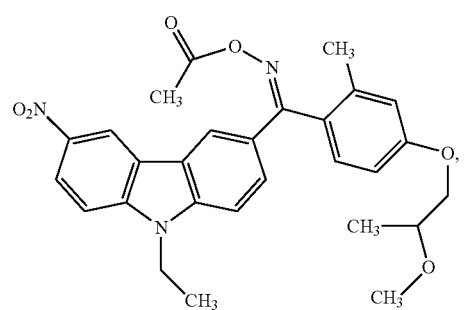
III-9
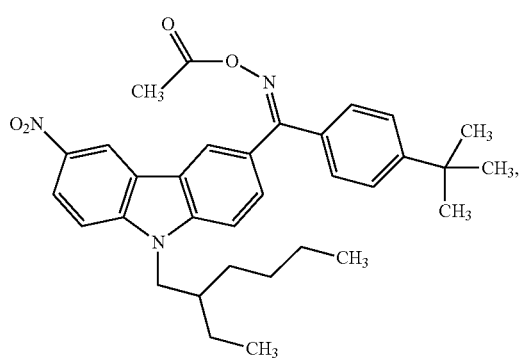
III-10
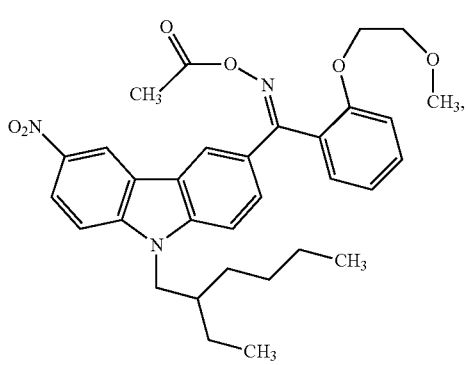
III-11
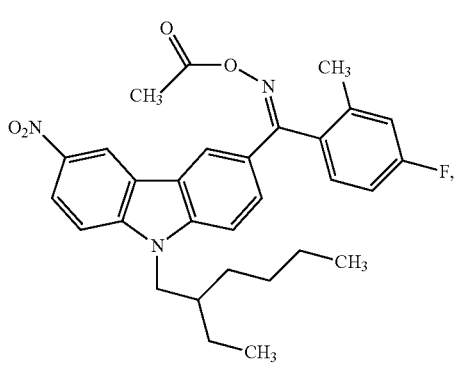
III-12
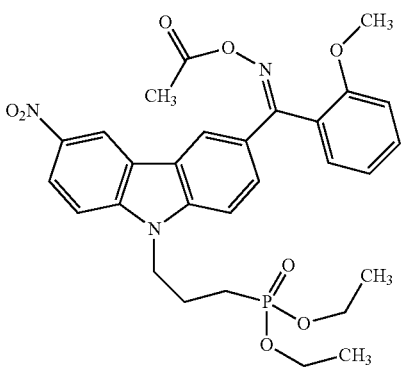
III-13
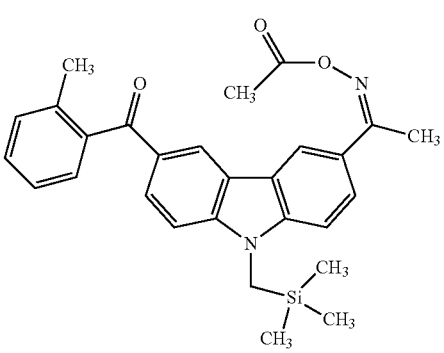
III-14
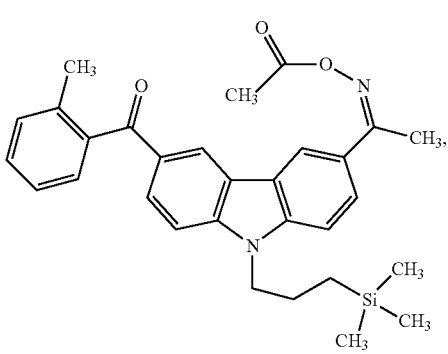
III-15
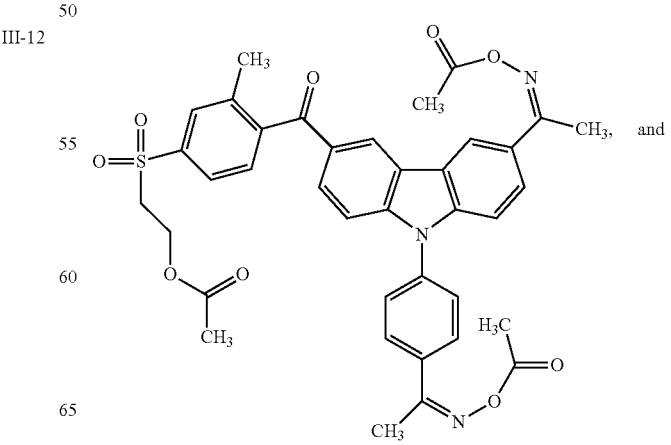
III-16
and III-17
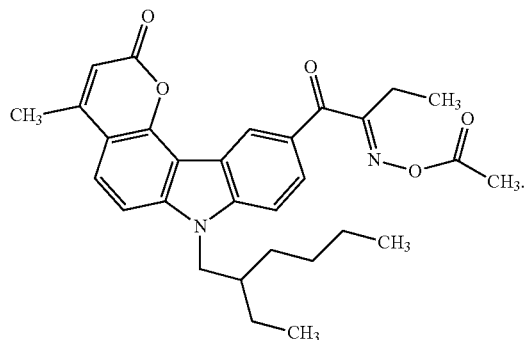
Preferably, the carbazolyl oxime ester of formulas IV-A to IV-E is selected from compounds of formulas IV-1 to IV-21 and any combination thereof:
IV-1
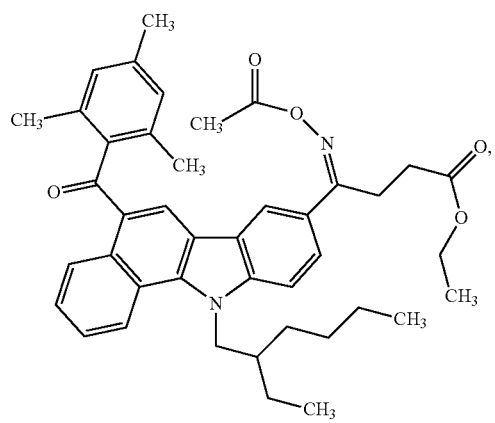
IV-2
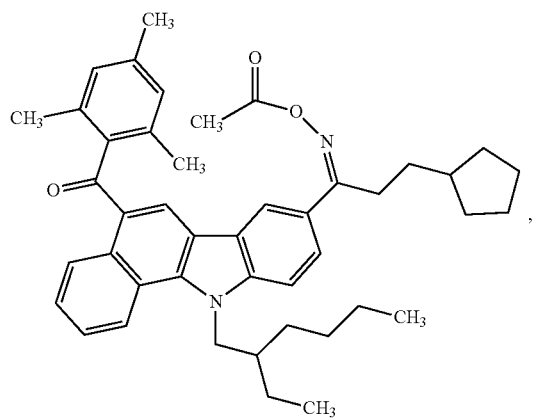
IV-3
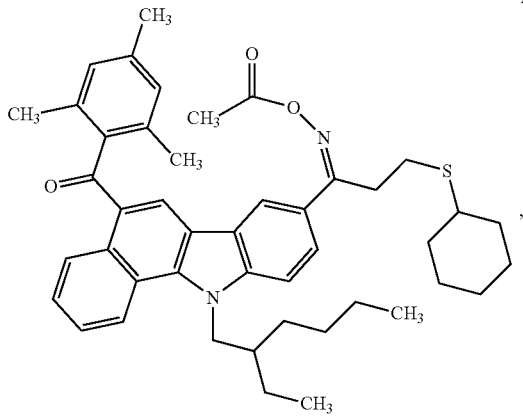
IV-4
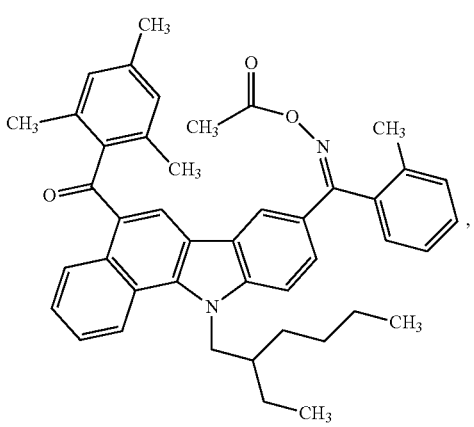
IV-5
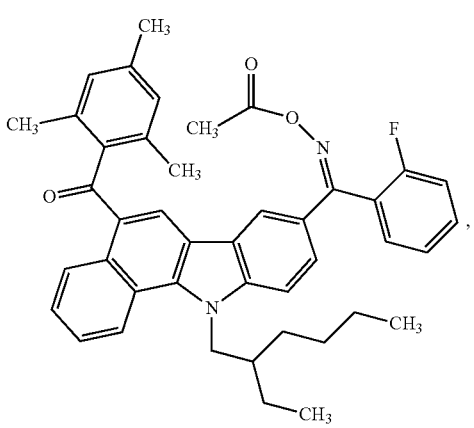

IV-6
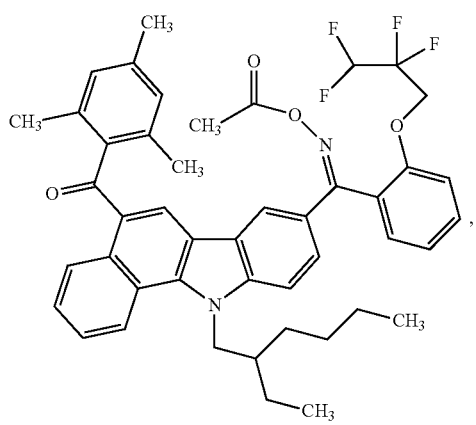
IV-7
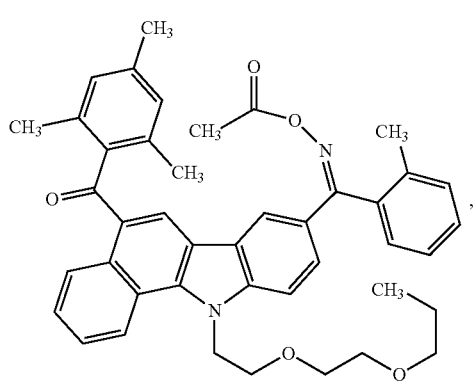
IV-8
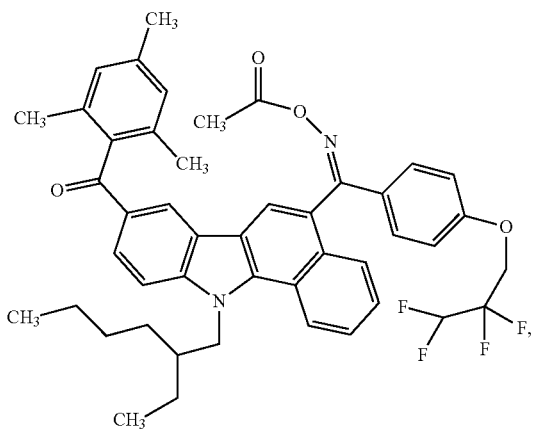
IV-9
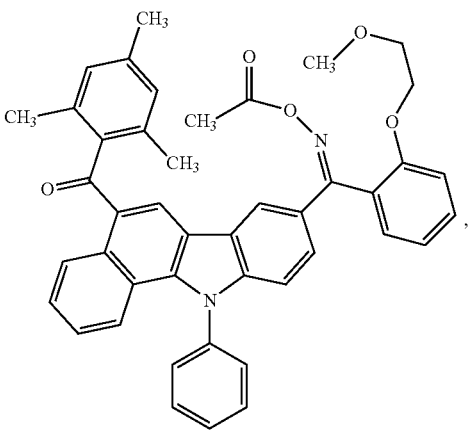
IV-10
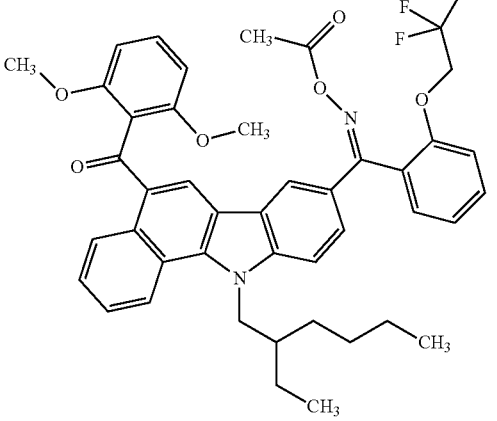
IV-11
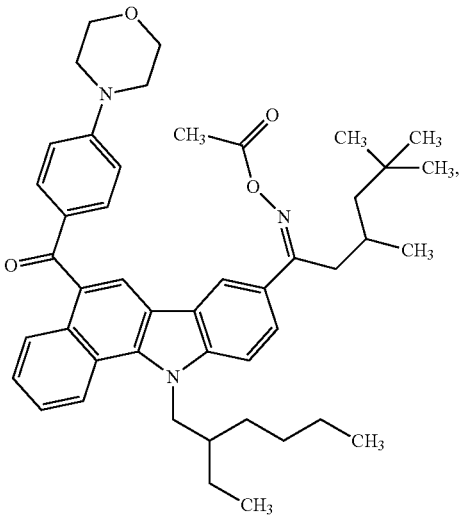

IV-12
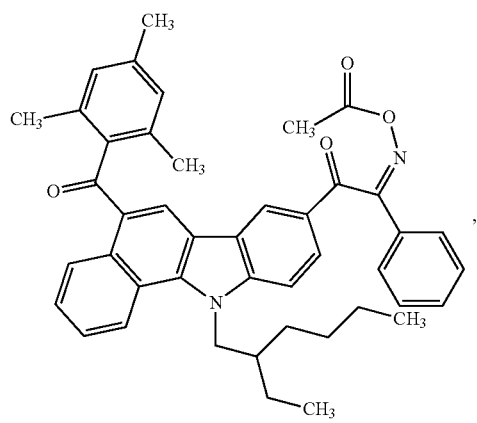
IV-13
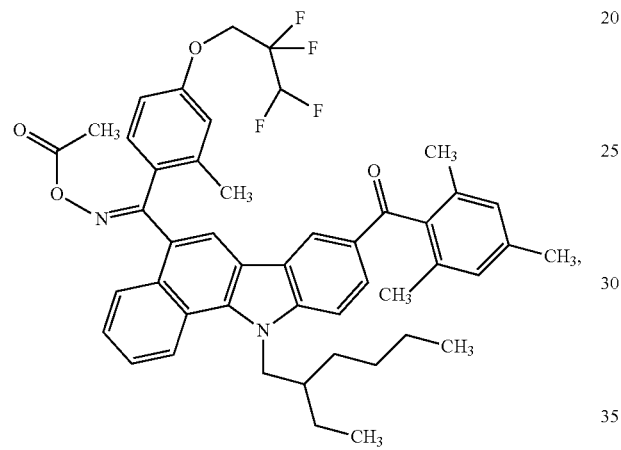
IV-14
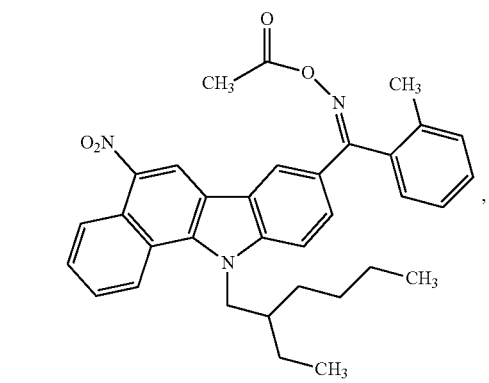
IV-15
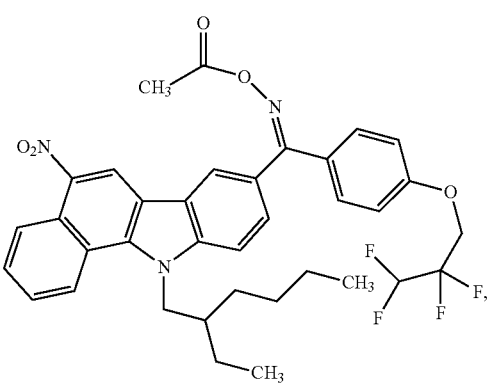
IV-16
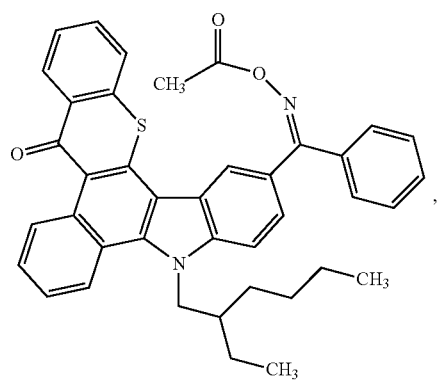
IV-17
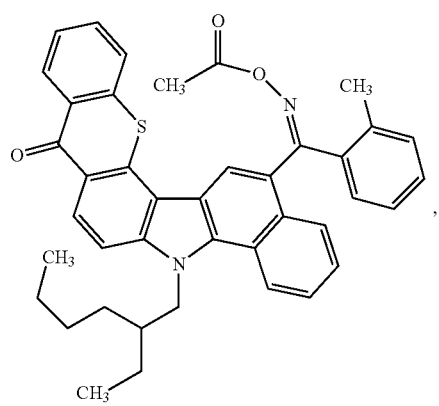
IV-18
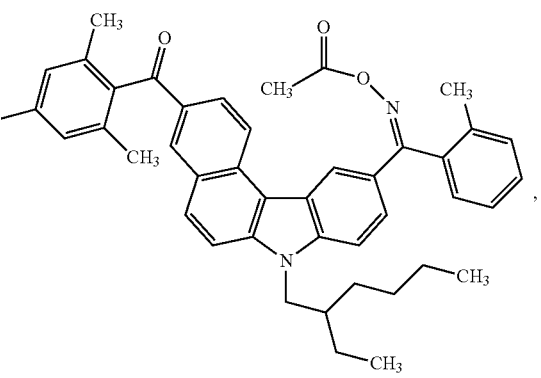
IV-19
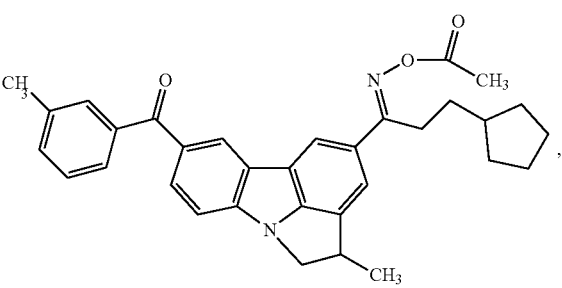

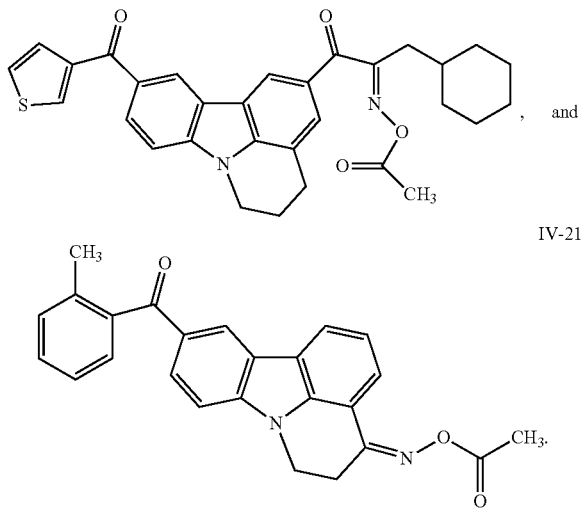

Preferably, the acylcarbazole derivatives of formulas I, II-A to II-E and II-G are prepared as follows: preparing an acylation product via one-step or two-step Friedel-Crafts acylation reaction by reacting a corresponding substituted carbazole or benzocarbazole with a corresponding acylation reagent such as acyl chloride or acid anhydride; and performing further reactions with corresponding reagents when the aroyl or heteroaroyl has active substituents that needs further reactions. For example, fluorine atom can be substituted by an alkoxy, alkyl sulphanyl, secondary amino, phenoxyl, thiophenyl or similar reagents, or carboxylic acid and an alcohol compound undergo an esterification reaction, etc., to obtain the final compounds of formulas I, II-A to II-E and II-G.

Preparation method of II-F comprises: preparing a N-(carboxyphenyl)carbazole derivative intermediate via N-substitution reaction between corresponding 1-position and 9-position unsubstituted carbazole compounds and o-bromobenzoic acide, and carrying out ring-forming condensation reaction with the intermediate under the catalysis of acid such as concentrated sulfuric acid or polyphosphoric acid, obtaining II-F.

Preparation method of II-H comprises: (1) carrying out N-alkylation reaction between corresponding 1-position, 6-position and 9-position unsubstituted carbazole compounds as raw materials and bromocarboxylic acid; (2) carrying out a condensation reaction, or carboxylic acid chloride acetylation in the presence of an acid catalyst followed by Friedel-Crafts acylation reaction to obtain a bicyclic carbazole derivative; and (3) carrying out Friedel-Crafts acylation reaction to obtain II-H.

The carbazolyl oxime ester can be prepared for example via oximation and esterification using corresponding acylcarbazole parent compounds as a raw material.

In a second aspect, provided is a method for preparing a photoinitiator composition, comprising: well mixing 0.1 mol of a sensitizing agent compound such as a compound of formula I-34 with 0.1 mol of a carbazolyl oxime ester such as a compound of formula IV-6 to obtain a photoinitiator composition. Alternatively, the photoinitiator composition can be prepared by directly mixing one or more sensitizing agent compounds with one or more carbazolyl oxime esters and other components, wherein a ratio of the total molar amount of the sensitizing agent to a total molar amount of the carbazolyl oxime ester is not greater than 2:1, preferably is 0.1:1 to 1.4 1, and more preferably is 0.22:1 to 1.3:1.

In a third aspect, the present invention further provides a photocurable composition, comprising:
 a. a photoinitiator composition, comprising at least one sensitizing agent of any one of formulas I, and II-A to II-H and at least one carbazole oxime ester compound of any one of formulas formula III, and IV-A to IV-F; optionally, component a accounts for 0.2-10%, preferably 1-8% by weight of a total weight of all solids in the formulation; and
 b. at least one radically polymerizable compound; optionally, the radically polymerizable compound is selected from the group consisting of an acrylate compound, a methacrylate compound, a resin containing acrylate or methacrylate groups, and any combination thereof.

Preferably, as for the radically polymerizable compounds, examples of compounds having a low molecular weight include alkyl acrylate, cycloalkyl acrylate, hydroxyalkyl acrylate, dialkylaminoalkyl acrylate, alkyl methacrylate, cycloalkyl methacrylate, hydroxyalkyl methacrylate, and dialkylaminoalkyl methacrylate, such as methyl acrylate, butyl acrylate, cyclohexyl acrylate, 2-hydroxyethyl acrylate, isobornyl acrylate, ethyl methacrylate, and polysiloxane acrylate; other examples include acrylonitrile, vinyl acetate, vinyl ether, styrene, and N-vinyl-2-pyrrolidone. Examples of compounds containing two or more double bonds include ethylene glycol, polyethylene glycol, propylene glycol, neopentyl glycol, diacrylate of 1,6-hexanediol, trihydroxymethane triacrylate, pentaerythritol tetraacrylate, dipentaerythritol hexaacrylate, vinyl acrylate, triallyl isocyanurate, etc. Examples of double bond compounds having a higher molecular weight include a large class of substances commonly known as oligomers generally having a molecular weight of 500-3000, such as acrylated epoxy resin, acrylated polyester resin unsaturated polyester resin, acrylated polyether resin, and acrylated polyurethane resin.

In a fourth aspect, the present invention also provides an ink or a coating, which comprises the above-mentioned photocurable composition, into which other necessary components can also be added depending on the required performance such as ink color, printing application, etc. The ink or coating can be used for pattern printing, 3D printing, PCB solder mask, liquid or dry film corrosion resistant materials, substrate protective coating, etc.

In a fifth aspect, the present invention also provides an adhesive, which comprises the above-mentioned photocurable composition, into which other necessary components can also be added depending on the required performance for the adhesive. The adhesive can be used for adhering glass, plastic, metal members, etc.

In addition to the materials listed herein, it is easy for those skilled in the art to add other necessary ingredients, such as stabilizers, surfactants, leveling agents and dispersants, according to the existing technology and use of the photocurable composition.

In a sixth aspect, the present invention also provides a photoresist, comprising:
 a. at least one of the above photoinitiator composition, the mass of which accounts for 0.2% to 10%, preferably 1% to 8% by weight of a total weight of all solids in the formulation;
 b. a multifunctional acrylate monomer,
 c. an alkali-soluble resin,
 d. a pigment, and
 e. a solvent.

Examples of the multifunctional acrylate monomer in component b include: dipentaerythritol hexaacrylate and pentaerythritol tetraacrylate. Examples of the alkali soluble resin in component c include copolymers obtained by copolymerizing of polyacrylate having a carboxylic acid group, such as methacrylic acid, itaconic acid, maleic acid, etc., and a common monomer such as methyl acrylate, butyl methacrylate, benzyl acrylate, hydroxyethyl acrylate, styrene, butadiene, maleic anhydride, etc. Preferred examples of the copolymer include a copolymer of methyl methacrylate and methacrylic acid, a copolymer of benzyl methacrylate and methacrylic acid, a copolymer of methyl methacrylate, butyl methacrylate, methacrylic acid and styrene.

Examples of the pigment in component d include: C.I. pigment red 177, C.I. pigment green 7, C.I. pigment blue 15:6, solvent blue 25, carbon black, titanium black, and C.I. pigment black 1.

Component b, component c, component d and component e are described in many existing literatures such as CN103153952A, and those skilled in the art can make selections according to their needs.

In addition to the component a as a photoinitiator, other existing or commercial available photoinitiators or co-initiators, such as Omnirad BDK, Omnirad 369, Omnirad 379, Omnirad 389, Omnirad TPO, Omnirad 819, Omnirad ITX, Omnirad DETX, and Omnirad 784, can also be added, as long as it is beneficial to the performance of the photocurable composition, especially the photoresist, wherein, Omnirad is a commodity of IGM resin company.

In addition to the above components, other resins such as polyalkyl methacrylate, ethyl cellulose, carboxymethyl cellulose, linear phenolic resin, polyvinyl butyral, polyvinyl acetate, polyester and polyimide can be added.

In a seventh aspect, the present invention also provides a black photoresist. When the pigment in the photoresist is a well-dispersed black pigment such as carbon black or titanium black, it becomes a black photoresist. Black photoresist can be used to prepare a black matrix, a spacer of cell gap, and a microlens.

In an eighth aspect, a color filter device can be prepared by a color filter processing process using the photoresist and/or black photoresist of the present invention as raw materials, which is an important component of a color display screen.

Further provided is any article such as a color filter and a color display screen prepared by necessary processes using any materials comprising the photoinitiator composition of the present invention.

DETAILED DESCRIPTION OF EMBODIMENTS

The following non-limiting embodiments and comparative examples are provided for illustrating the present invention in details.

Light Source Apparatus:
365 nm LED surface light source, Lantian Special Light Development Co., Ltd.
Testing Equipment:
Stereo microscope, COVS-50G, Guangzhou Mingmei Optoelectronic Technology Co., Ltd.
Experimental Materials:
A compound of formula of I-1: from compound preparation example 3;
A compound of formula of I-27: from compound preparation example 4;
A compound of formula of I-34: from compound preparation example 1;
A compound of formula of II-1: from compound preparation example 5;
A compound of formula of II-3: from compound preparation example 6;
A compound of formula of II-5: from compound preparation example 2;
Omnirad DETX: a photoinitiator product of IGM Resin Company;
Esacure 3644: a photoinitiator product of IGM Resin Company;
Omnirad EMK: a photoinitiator product of IGM Resin Company;
OXE 02: a compound of formula of III-1: a photoinitiator product of BASF Company;
OXE 03: a compound of formula of IV-6: a photoinitiator product of BASF Company;
NCI 831: a compound of formula of III-9: a product of ADEKA Company, Japan;
PBG 304: a compound of formula of III-2: a product of Changzhou Qiangli Electronic New Material Co., Ltd.;
Photomer 6010: aliphatic urethane triacrylate, a product of IGM Resin Company, Netherlands;
DPHA: dipentaerythritol penta/hexaacrylate, a product of Tianjin Tianjiao Chemical Co., Ltd.;
HPMA: polymaleic acid, a product of Aladdin Industries, USA.

PREPARATION EXAMPLES

Preparation of Acylcarbazole Derivatives

Compound Preparation Example 1 Preparation of 9-ethyl-3,6-bis[4-(2,2,3,3-tetrafluoropropoxy)benzoyl]carbazole (A Compound of Formula I-34)

1a. 9-ethyl-3,6-bis(4-fluorobenzoyl)carbazole
19.5 g of N-ethyl carbazole is dissolved in 250 mL of dichloroethane, and 34 g of aluminum trichloride is added to obtain a solution. The temperature is kept at 0~-5° C., and 40 g of p-fluorobenzoyl chloride is added dropwise into the solution, then the temperature is kept at 0~5° C. to react for 15 h. The reaction solution is added into 100 mL of 10% HCl solution of 0° C. in batches, followed by stirring for 30 min. After standing for 30 min, a dichloroethane phase is separated and washed with 50 mL of 2% sodium hydroxide solution for 30 min. The dichloroethane solution is vacuum distilled to recover dichloroethane. The residue is crystallized by adding 80 mL of ethyl acetate to obtain 30.5 g of a product as a white powder having a content of 98.5% and a yield of 69.5%.

1b. 9-ethyl-3,6-bis[4-(2,2,3,3-tetrafluoropropoxy)benzoyl]carbazole
30 g of 9-ethyl-3,6-bis(4-fluorobenzoyl) carbazole prepared in step 1a, 25 g of 2,2,3,3-tetrafluoropropanol and 8 g of sodium hydroxide are dissolved in 200 mL of pyridine and reacted at 70° C. for 18 h. Vacuum distillation is carried out to evaporate pyridine and redundant 2,2,3,3-tetrafluoropropanol. 100 ml of water and 250 mL of dichloroethane are added to the residue and stirred for 1 h. Then an aqueous phase is separated. The dichloroethane solution is washed twice with 100 mL of water, and vacuum distilled to recover dichloroethane. 150 mL of ethyl acetate and 2 g of activated carbon are added to the residue, followed by refluxing under heating for 1 h and filtering to remove activated carbon to obtain a filtrate. The filtrate is vacuum distilled to remove about 100 ml of ethyl acetate, then cooled to crystallize, and filtered. The filter cake is dried to obtain 27.8 g of a product as a light yellow powder having a content of 98.5% and a yield of 61.4%.

The structure is confirmed by $^1$H-NMR spectrum (CDCl$_3$), δ[ppm]: 1.512 (t, 3H), 4.425-4.483 (m, 6H), 5.949-6.277 (m, 2H), 7.016-7.045 (m, 4H), 7.496-7.517 (d, 2H), 7.844-7.868 (d, 4H), 7.990-8.011 (d, 2H), 8.534 (s, 2H).

Compound Preparation Example 2: Preparation of 11-(2-ethylhexyl)-5,8bis[4-(2,2,3,3-tetrafluoropropoxy)benzoyl]-11H-benzo[a]carbazole (A Compound of Formula II-5)

2a. 11-(2-ethylhexyl)-5,8-bis(4-fluorobenzoyl)-11H-benzo[a]carbazole 2.0 g of B03D is added into to a 50 mL single-necked flask, and 20 mL of dichloroethane is added to dissolve it, then 0.2 g of zinc chloride and 2.3 g of o-fluorobenzoyl chloride are added, and stirred and reacted at 80° C. for 10 h. After cooling, the reaction solution is washed twice with 20 mL of water, and then concentrated under reduced pressure to dryness to obtain 4.0 g of a brown viscous substance, which is used in the reaction of 2b without purification.

2b. 11-(2-ethylhexyl)-5,8bis[4-(2 2,3,3-tetrafluoropropoxy)benzoyl]-11H-benzo[a]carbazole 4.0 g of 11-(2-ethylhexyl)-5,8-bis(4-fluorobenzoyl)-11H-benzo[a]carbazole obtained in step 2a is dissolved with 20 mL pyridine in a 50 mL single-necked flask, then 2.2 g of tetrafluoropropanol and 1.2 g of sodium hydroxide are added, heated to 80° C. and stirred for 5 h. The reaction solution is added dropwise to 100 ml of water, then stirred with 100 mL of dichloroethane for 1 h, and allowed to stand for separation. The separated dichloroethane solution is concentrated under reduced pressure to dryness to obtain 4.7 g of brown solid. The brown solid is dissolved under heating in a mixed solvent of 20 mL ethyl acetate and 20 mL ethanol, then 0.25 g activated carbon is added, followed by refluxing for 1 h. The resulted solution is hot filtered, and the filtrate is cooled down to precipitate a yellow crystal, which is dried to obtain 2.5 g product. The total yield of the two-step reaction is 51.3%, and the content of 11-(2-ethylhexyl)-5,8bis[4-(2,2,3,3-tetrafluoropropoxy)benzoyl]-11H-benzo[a]carbazole is 98.51%.

The structure is confirmed by $^1$H-NMR spectrum (CDCl$_3$), δ[ppm]: 0.754-0.789 (m, 6H), 1.126-1.328 (m, 8H), 2.113 (s, 1H), 4.369-4.452 (t, 2H), 4.513-4.599 (t, 2H), 4.928 (m, 2H), 4.994-5.342 (m, 1H), 5.537-5.885 (m, 1H), 7.251-7.272 (m, 4H), 7.430-7.455 (d, 1H)), 7.566-7.811 (m, 6H), 7.950-7.979 (d, 1H), 8.430 (s, 1H), 8.571 (s, 1H), 8.668-8.695 (d, 1H), 8.736-8.764 (d, 1H)).

Compound Preparation Example 3: Preparation of 3-(2-methylbenzoyl)-9-ethylcarbazole (A Compound of Formula I-1)

The operation as described in step 1.a in example 1 on page 81 of the specification of CN100528838C is incorporated by reference. Wherein, o-methylbenzoyl chloride is used instead of benzoyl chloride. 5.88 g (44.1 mmol) of AlCl$_3$ is added to 7.83 g (40.1 mmol) of N-ethylcarbazole in 40 mL of CH$_2$Cl$_2$ to obtain a solution. The temperature is kept at below 10° C., and 6.5 g (42 mmol) o-methylbenzoyl chloride is added dropwise into the solution, followed by stirring for 4 h at room temperature to obtain a reaction mixture. Then, the reaction mixture is added dropwise into hydrochloric acid-containing ice-water. An organic phase is separated, washed with water until the pH is 7, dried over anhydrous MgSO4, purified by silica gel column chromatography with dichloromethane-hexane (1:1) as eluent, obtaining 9.45 g of a white solid having a yield of 75.1% and a content of 98.51%.

The structure is confirmed by $^1$H-NMR spectrum (CDCl$_3$), δ[ppm]: 1.431/1.455/1.479 (t, 3H); 2.349 (s, 3H); 4.352/4.376/4.400/4.424 (quartet, 2H); 7.246-7.530 (m, 8H); 7.989/7.994/8.018/8.023 (dd, 1H); 8.065/8.090 (d, 1H); 8.561/8.564 (d, 1H).

Compound Preparation Example 4: Preparation of 3,6-bis(2-methylbenzoyl)-9-(3-methylbutyl)carbazole (A Compound of Formula I-27)

4.5 g (19 mmol) of N-(3-methylbutyl) carbazole is dissolved in 20 mL of 1,2-dichloroethane, and the temperature is cooled to −5° C. in a low temperature bath, followed by adding 5.3 g (40 mmol) of anhydrous AlCl$_3$. Then, a solution comprising 6.0 g (38.8 mmol) of o-methylbenzoyl chloride and 10 g of dichloroethane is added dropwise therein. The temperature is kept at 5° C. to react for 3 h. The reaction solution is added dropwise to 20 ml of concentrated hydrochloric acid and 40 ml of water having a temperature not exceeding 10° C., followed by stirring for 30 min. After standing, an organic phase is separated, washed with 80 ml of water until the pH is 7, and concentrated under a reduced pressure to remove dichloroethane, obtaining 10.0 g of light yellow vitreous substance. 150 ml of absolute ethanol is added to completely dissolve the vitreous substance under refluxing and heating. The resulted solution is cooled to precipitate a crystal, followed by filtration to give a filter cake which is then dried to obtain 8.0 g of white powder. HPLC analysis shows the content is 98.53%, and the yield is 96.4%.

The structure is confirmed by $^1$H-NMR spectrum (CDCl$_3$), δ[ppm]: 1.031/1.052 (d, 6H); 1.681-1.815 (m, 3H); 2.344 (s, 6H); 4.347/4.374/4.397 (t, 2H)); 7.289-7.467 (m, 10H); 8.018/8.023/8.047/8.052 (dd, 2H); 8.535/8.540 (s, 2H).

Compound Preparation Example 5: Preparation of 5-(2,4,6-trimethylbenzoyl)-11-(2-ethylhexyl)-11H-benzo[a]carbazole (Compound of Formula II-1)

The operation as described in step (a) in example 18 on page 63 of the specification of CN103153952A is incorporated by reference. In a 1 L reaction flask, 47.16 g (143.0 mmol) of 11-(2-ethylhexyl)-11H-benzo[a]carbazole is dissolved in 400 ml CH$_2$Cl$_2$ to obtain a solution. 20.0 g (150 mmol) of AlCl$_3$ is added thereto. The temperature is kept at 0° C., and 27.45 g (150 mmol) of 2,4,6-trimethylbenzoyl chloride is added dropwise to the solution, followed by stirring for 2 h at room temperature to obtain a reaction mixture. Then, the reaction mixture is poured into ice-water, and a CH$_2$Cl$_2$ solution phase is separated. The aqueous phase is extracted twice with CH$_2$Cl$_2$. The organic phases are combined and washed with water until the pH is 7, and dried over MgSO$_4$. After most CH$_2$Cl$_2$ is removed by concentration, 230 ml of n-hexane is added therein to precipitate a beige solid. The solid is dried under a reduced pressure to obtain 65.0 g of a product having a content of 99.1% and a yield of 95.6%. $^1$H-NMR spectrum confirms that the product is 5-(2,4,6-trimethylbenzoyl)-11-(2-ethylhexyl)-11H-benzo[a]carbazole, δ[ppm, CDCl$_3$]: 0.805/0.823/0.841 (t, 3H); 0.872/0.891/0.909 (t, 3H); 1.184-1.408 (m, 9H); 2.198 (s, 6H); 2.390 (s, 3H); 4.670-4.785 (m, 2H);

6.946 (s, 2H); 7.271/7.288 (d, 1H); 7.450/7.453//7.471/7.474//7.489/7.491 (dt, 1H); 7.550/7.571 (d, 1H); 7.667/7.670//7.684/7.687/7.691//7.705/7.709 (dt, 1H); 7.720/7.724//7.738/7.742/7.746//7.759/7.762 (dt, 1H); 7.939/7.958 (d, 1H); 8.361 (s, 1H); 8.643/8.662 (d, 2H); 9.629/9.632//9.650/9.653 (dd, 1H).

Compound Preparation Example 6: Preparation of 5-(2,4,6-trimethylbenzoyl)-8-[2-(2,2,3,3-tetrafluoropropoxy)benzoyl]-11-(2-ethylhexyl)-11H-benzo[a] carbazole (A Compound of Formula II-3)

Part operations as described in steps 18.a and 18.b in example 18 on pages 63-64 of the specification of CN103153952A are incorporated by reference. Wherein, 2,2,3,3-tetrafluoro-1-propanol is used instead of 2-methoxyethanol to carry out the etherification reaction, and a etherification product is extracted to obtain a beige solid. $^1$H-NMR spectrum confirms that the solid is 5-(2,4,6-trimethylbenzoyl)-8-[2-(2,2,3,3-tetrafluoropropoxy)benzoyl]-11-(2-ethylhexyl)-11H-benzo[a]carbazole, δ[ppm, CDCl$_3$]: 0.795/0.819//0.843/0.870/0.894 (dt, 6H); 1.170-1.465 (m, 9H); 2.189 (s, 6H); 2.398 (s, 3H); 4.243/4.281/4.318 (t, 2H); 4.660-4.817 (m, 2H); 5.072/5.091/5.110//5.249/5.267/5.286//5.425/5.444/5.463 (tt, 1H); 6.958 (s, 2H); 6.958/6.989 (d, 1H); 7.158/7.183/7.207 (t, 1H); 7.456-7.549 (m, 3H); 6.682-7.795 (m, 3H); 8.362 (s, 1H); 8.607/8.611 (d, 1H); 8.621/8.649 (d, 1H); 9.540/9.544//9.568/9.572 (dd, 1H).

Composition Preparation Example 1

12 g of the compound of formula II-5 and 28 g of OXE-02 are mixed and ground in a mortar to obtain 40 g of a composition. A molar ratio of the acylcarbazole derivative to the carbazolyl oxime ester photoinitiator is 0.22:1.

Composition Preparation Example 2

12 g of the compound of formula I-34 and 28 g of OXE-02 are mixed and ground in a mortar to obtain 40 g of a composition. A molar ratio of the acylcarbazole derivative to the carbazolyl oxime ester photoinitiator is 0.27:1.

Composition Preparation Example 3

12 g of the compound of formula II-1 and 28 g of OXE-02 are mixed and ground in a mortar to obtain 40 g of a composition. A molar ratio of the acylcarbazole derivative to the carbazolyl oxime ester photoinitiator is 0.37:1.

Composition Preparation Example 4

12 g of the compound of formula I-27 and 28 g of OXE-03 are mixed and ground in a mortar to obtain 40 g of a composition. A molar ratio of the acylcarbazole derivative to the carbazolyl oxime ester photoinitiator is 0.75:1.

Composition Preparation Example 5

12 g of the compound of formula I-34 and 12 g of OXE-03 are mixed and ground in a mortar to obtain 24 g of a composition. A molar ratio of the acylcarbazole derivative to the carbazolyl oxime ester photoinitiator is 1.16:1.

Composition Preparation Example 6

12 g of the compound of formula II-5 and 28 g of OXE-03 are mixed and ground in a mortar to obtain 40 g of a composition. A molar ratio of the acylcarbazole derivative to the carbazolyl oxime ester photoinitiator is 0.41:1.

Preparation of Alkali-Soluble Resin 18 g of benzyl methacrylate, 6 g of methacrylic acid, 6 g of hydroxyethyl methacrylate, 1.5 g of azobisisobutyronitrile, 0.6 g of dodecanethiol, and 200 ml of toluene are added into a 1 L constant pressure dropping funnel. 100 ml of toluene is added into a 500 ml four-necked flask, air in the four-necked flask is replaced with nitrogen, and the temperature is increased to 80° C., then the solution in the funnel is added therein dropwise. After reacting for 6 h, the reaction solution is cooled down and filtered to obtain 24 g of a white alkali-soluble resin.

Preparation of Black Color Paste 50 g of the alkali-soluble resin, 50 g of P25 carbon black, 100 g of DPHA, and 250 g of propylene glycol methyl ether acetate are added into a 500 mL beaker, and mixed using a high-speed shear mixer at a speed of 3000 r/min for 15 min to obtain a black color paste.

Photoresist Examples 1-14 and Comparative Examples 1-14

The examples and comparative examples are prepared according to the components described in tables 1 to 4.

The compositions prepared in the composition preparation examples can be used as the initiator and sensitizing agent, or can be mixed according to the proportion in the table and dissolved in the PMA, and then the composition solution is mixed with the black color paste in proportion. After the components are mixed well, the resulted is coated onto a glass slide using a 10 μm wire rod, and put into an oven for drying at 90° C. for 5 min. A 365 nm light source is used to perform curing with a mask, and then development is carried out using a 1% NaOH solution at 25° C., followed by soaking and cleaning for 10 s with pure water. After drying in an oven at 90° C. for 30 minutes, the line width of the developed image is measured.

TABLE 1

| | Examples | | | Comparative examples | | | |
| --- | --- | --- | --- | --- | --- | --- | --- |
| | 1 | 2 | 3 | 1 | 2 | 3 | 4 |
| OXE 02 | 0.056 | 0.04 | 0.032 | 0.08 | 0.056 | 0 | 0.024 |
| Compound of formula II-1 | 0.024 | 0.04 | 0.048 | 0 | 0 | 0.08 | 0.056 |
| PMA | 2 | 2 | 2 | 2 | 2 | 2 | 2 |
| black color paste | 4.5 | 4.5 | 4.5 | 4.5 | 4.5 | 4.5 | 4.5 |
| sensitizing agent/initiator molar ratio | 0.37 | 0.87 | 1.3 | 0 | 0 | 0 | 2.02 |

TABLE 2

| | Examples | | Comparative examples | | |
| --- | --- | --- | --- | --- | --- |
| | 4 | 5 | 1 | 5 | 6 |
| OXE 02 | 0.056 | 0.04 | 0.08 | 0 | 0.024 |
| Compound of formula I-34 | 0.024 | 0.04 | 0 | 0.08 | 0.056 |
| PMA | 2 | 2 | 2 | 2 | 2 |

TABLE 2-continued

|  | Examples | | Comparative examples | | |
|---|---|---|---|---|---|
|  | 4 | 5 | 1 | 5 | 6 |
| black color paste | 4.5 | 4.5 | 4.5 | 4.5 | 4.5 |
| sensitizing agent/initiator molar ratio | 0.27 | 0.62 | 0 | 0 | 1.45 |

TABLE 3

|  | Examples | | | | Comparative examples | | |
|---|---|---|---|---|---|---|---|
|  | 6 | 7 | 8 | 9 | 7 | 8 | 9 |
| OXE 03 | 0.056 | 0.04 | 0.056 | 0.04 | 0.08 | 0.024 | 0.024 |
| Compound of formula I-34 | 0.024 | 0.04 | 0 | 0 | 0 | 0.056 | 0 |
| Compound of formula II-5 | 0 | 0 | 0.024 | 0.04 | 0 | 0 | 0.056 |
| PMA | 2 | 2 | 2 | 2 | 2 | 2 | 2 |
| black color paste | 4.5 | 4.5 | 4.5 | 4.5 | 4.5 | 4.5 | 4.5 |
| sensitizing agent/initiator molar ratio | 0.49 | 1.16 | 0.41 | 0.96 | 0 | 2.69 | 2.24 |

TABLE 4

|  | Examples | | | | Comparative examples | | | |
|---|---|---|---|---|---|---|---|---|
|  | 10 | 11 | 12 | 13 | 1 | 10 | 11 | 12 |
| OXE 02 | 0.056 | 0.056 | 0.056 | 0.056 | 0.08 | 0.056 | 0.056 | 0.056 |
| Compound of formula I-27 | 0.024 | 0 | 0 | 0 | 0 | 0 | 0 | 0 |
| Compound of formula II-5 | 0 | 0.024 | 0 | 0 | 0 | 0 | 0 | 0 |
| Compound of formula II-3 | 0 | 0 | 0.024 | 0 | 0 | 0 | 0 | 0 |
| Compound of formula I-1 | 0 | 0 | 0 | 0.024 |  |  |  |  |
| Omnirad DETX | 0 | 0 | 0 | 0 | 0 | 0.024 | 0 | 0 |
| Esacure3644 | 0 | 0 | 0 | 0 | 0 | 0 | 0.024 | 0 |
| Omnirad EMK | 0 | 0 | 0 | 0 | 0 | 0 | 0 | 0.024 |
| PMA | 2 | 2 | 2 | 2 | 2 | 2 | 2 | 2 |
| black color paste | 4.5 | 4.5 | 4.5 | 4.5 | 4.5 | 4.5 | 4.5 | 4.5 |
| sensitizing agent/initiator molar ratio | 0.37 | 0.22 | 0.25 | 0.56 | 0 | 0.66 | 0.21 | 0.54 |

TABLE 5

|  | Example 14 | Example 15 | Comparative example 13 | Comparative example 14 |
|---|---|---|---|---|
| NCI 831 | 0.056 | 0 | 0.08 | 0 |
| PBG 304 | 0 | 0.056 | 0 | 0.08 |
| Compound of formula I-34 | 0.024 | 0.024 | 0 | 0 |
| PMA | 2 | 2 | 2 | 2 |
| black color paste | 4.5 | 4.5 | 4.5 | 4.5 |
| sensitizing agent/initiator molar ratio | 0.27 | 0.23 | 0 | 0 |

The examples and comparative examples in table 1 are used to perform coating, curing, developing, and measuring. The data are shown in table 6. The results show that: examples where OXE 02 is used as an initiator, and the compound of formula II-1 is used as a sensitizing agent at a ratio within the range of the present invention exhibit significantly greater developing line width values than the corresponding comparative examples, and exhibit significantly better sensibilization than comparative examples in which a sensitizing agent is not used, or a sensitizing agent is used alone or the amount of sensitizing agent is outside the range of the present invention. In particular, the results of comparative example 3 show that the compound of formula II-1 alone has almost no effect of initiating polymerization.

TABLE 6

|  | Examples | | | Comparative examples | | | |
|---|---|---|---|---|---|---|---|
|  | 1 | 2 | 3 | 1 | 2 | 3 | 4 |
| Break point/s | 20 | 19 | 19 | 20 | 20 | 15 | 19 |
| 120 μm Line width/μm | 135 | 129 | 122 | 119.58 | 103.78 | 0 | 115.12 |

The examples and comparative examples in table 2 are used to perform coating, curing, developing, and measuring. The data are shown in table 7. The results show that: examples where OXE 02 is used as an initiator, and the compound of formula I-34 is used as a sensitizing agent at a ratio within the range of the present invention exhibit significantly greater developing line width values than the corresponding comparative examples, and exhibit significantly better sensibilization than comparative examples in which a sensitizing agent is not used, or a sensitizing agent is used alone or the amount of sensitizing agent is outside the range of the present invention.

TABLE 7

|  | Examples | | Comparative examples | | |
|---|---|---|---|---|---|
|  | 4 | 5 | 1 | 5 | 6 |
| Break point/s | 20 | 20 | 20 | 20 | 20 |
| 120 μm Line width/μm | 135.81 | 127 | 119.58 | 0 | 104.17 |

The examples and comparative examples in table 3 are used to perform coating, curing, developing, and measuring. The data are shown in table 8. The results show that: examples where
OXE 03 is used as an initiator, and the compound of formula II-5 or I-34 is used as a sensitizing agent at a ratio within the range of the present invention exhibit significantly greater developing line width values than the corresponding comparative examples, and exhibit significantly better sensibilization than comparative examples in which a sensitizing agent is not used, or the amount of sensitizing agent is outside the range of the present invention.

TABLE 8

|  | Examples | | | | Comparative examples | | |
| --- | --- | --- | --- | --- | --- | --- | --- |
|  | 6 | 7 | 8 | 9 | 7 | 8 | 9 |
| Break point/s | 34 | 34 | 34 | 30 | 35 | 20 | 22 |
| 120 μm Line width/μm | 141.8 | 160.4 | 143.2 | 133.6 | 131.5 | 113.3 | 110.2 |

The examples and comparative examples in table 4 are used to perform coating, curing, developing, and measuring. The data are shown in table 9. The results show that: examples where
OXE 02 is used as an initiator, and the compound of formula I-27, II-5 or II-3 is used as a sensitizing agent exhibit significantly greater curing and developing line width values than the corresponding comparative examples, and exhibit significantly better sensibilization than comparative examples in which a sensitizing agent is not used or Esacure 3644, Omnirad DETX or EMK is used as a sensitizing agent.

TABLE 9

|  | Examples | | | | Comparative examples | | | |
| --- | --- | --- | --- | --- | --- | --- | --- | --- |
|  | 10 | 11 | 12 | 13 | 1 | 10 | 11 | 12 |
| Break point/s | 32 | 21 | 32 | 30 | 20 | 22 | 25 | 24 |
| 120 μm Line width/μm | 131 | 126 | 123 | 132 | 119 | 112 | 118 | 109 |

The examples and comparative examples in table 5 are used to perform coating, curing, developing, and measuring. The data are shown in table 10. The results show that: examples where NCI831 or PBG304 is used as an initiator, and the compound of formula I-35 is used as a sensitizing agent exhibit significantly greater curing and developing line width values than the corresponding comparative examples, and exhibit significantly better sensibilization than comparative examples in which a sensitizing agent is not used.

TABLE 10

|  | Examples | | Comparative examples | |
| --- | --- | --- | --- | --- |
|  | 14 | 15 | 13 | 14 |
| Break point/s | 32 | 25 | 30 | 22 |
| 120 μm Line width/μm | 163 | 130 | 138 | 115 |

Adhesive Examples 16, 17 and Comparative Example 15

The examples and comparative examples are prepared according to the components described in table 11. After the components are mixed well, they are coated onto a glass slide using a 50 μm wire rod to form a film, which is then cured under a 365 nm light source with a mask. After curing, the film weight is measured. After immersing in acetone at room temperature for 36 h, the film weight is measured again, and the gel conversion rate is calculated.

TABLE 11

|  | Example 16 | Example 17 | Comparative example 15 |
| --- | --- | --- | --- |
| Photomer 6010 | 5 | 5 | 5 |
| HPMA | 4.5 | 4.5 | 4.5 |
| OXE 02 | 0 | 0 | 0.5 |
| Composition preparation example 1 | 0.5 | 0 | 0 |
| Composition preparation example 2 | 0 | 0.5 | 0 |

Test data of the comparative examples and examples in table 11 are shown in Table 12. The data show that the adhesives in embodiments 16 and 17 in which the photocurable composition of the present inventions are used have significantly higher gel conversion rate under lights than that in comparative example 15 in which oxime ester photoinitiator is used alone.

TABLE 12

|  | Example 16 | Example 17 | Comparative example 15 |
| --- | --- | --- | --- |
| Gel conversion rate | 92.5% | 92.7% | 85.2% |

In summary, in the present invention, the photoinitiator composition comprising an acylcarbazole derivative and a carbazolyl oxime ester shows a significant higher curing activity than the corresponding photoinitiator composition in which the same kind of carbazolyl oxime ester is used alone. The best sensitising effect is shown when the molar ratio of the acylcarbazole derivatives to the carbazolyl oxime ester is 0.1 to 1.4.

The invention claimed is:

1. A photoinitiator composition comprising a sensitizing agent and a carbazolyl oxime ester, wherein the sensitizing agent is selected from the group consisting of acylcarbazole derivatives of formula I, acyl benzocarbazole derivatives of formula II-A, II-B or II-C, acyl dibenzocarbazole derivatives of formula II-D or II-E, and bicyclic carbazole derivatives of formula II-F, II-G or II-H, and wherein the carbazolyl oxime ester is selected from the group consisting of compounds of formulas III and IV-A to IV-E:

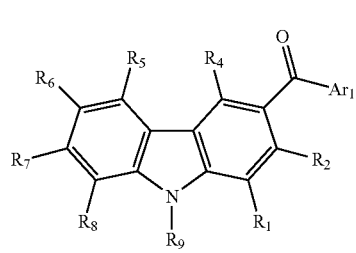

I

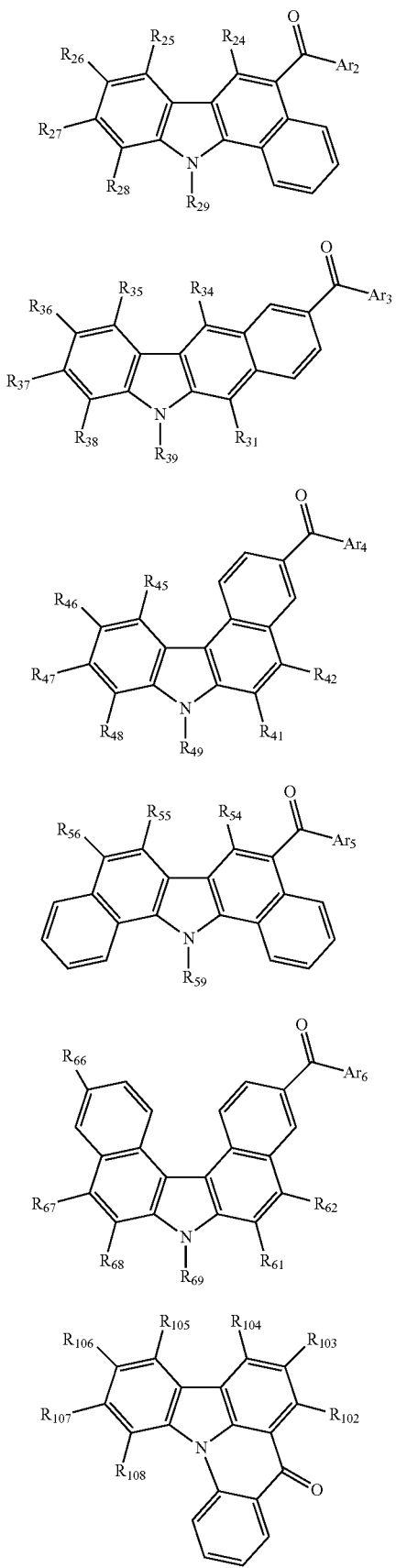

-continued

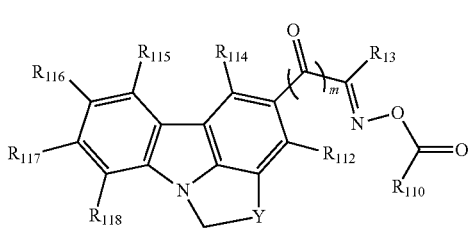

IV-D

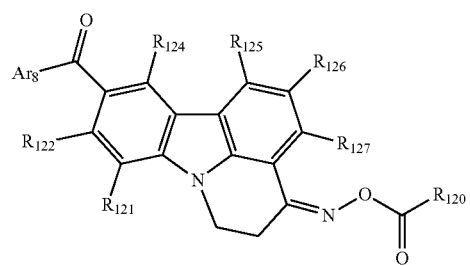

IV-E wherein,
$R_1$, $R_2$, $R_4$, $R_5$, $R_7$, $R_8$, $R_{24}$, $R_{25}$, $R_{27}$, $R_{28}$, $R_{34}$, $R_{35}$, $R_{37}$, $R_{38}$, $R_{41}$, $R_{42}$, $R_{44}$, $R_{45}$, $R_{47}$, $R_{48}$, $R_{54}$, $R_{55}$, $R_{61}$, $R_{62}$, $R_{67}$, $R_{68}$, $R_{102}$-$R_{108}$, $R_{112}$, $R_{114}$, $R_{115}$, $R_{117}$, $R_{118}$, $R_{121}$, $R_{122}$ and $R_{124}$-$R_{127}$ are each independently selected from the group consisting of H, halogen, C1-C8 alkyl, C1-C8 alkoxy, and CN;

$R_{11}$, $R_{12}$, $R_{14}$, $R_{15}$, $R_{17}$, $R_{18}$, $R_{71}$, $R_{72}$, $R_{74}$, $R_{75}$, $R_{84}$, $R_{85}$, $R_{87}$, $R_{88}$, $R_{91}$, $R_{92}$, $R_{94}$, $R_{97}$ and $R_{98}$ are each independently selected from the group consisting of H, C1-C8 alkyl, C1-C8 alkoxy, halogen, CN and $NO_2$;

$R_6$, $R_{26}$, $R_{36}$, $R_{46}$, $R_{56}$, $R_{66}$, $R_{106}$ and $R_{116}$ each independently selected from the group consisting of H, halogen, CN, C1-C8 alkyl, C1-C12 alkyl acyl, C5-C6 substituted C1-C3 alkyl acyl, C6-C20 aroyl, C4-C20 heteroaryl acyl,

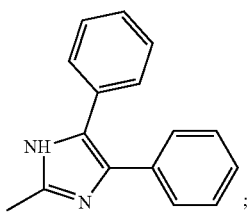 [SMILES: Cc1nc(-c2ccccc2)c(-c2ccccc2)[nH]1]

or wherein the above groups can optionally be connected with other adjacent substituents together with the parent structure to form a five-membered to seven-membered ring; wherein the C6-C20 aroyl and the C4-C20 heteroaryl acyl are independently substituted by substituents selected from the group consisting of H, halogen, $R_{40}$, $OR_{50}$, $SR_{50}$, $NR_{51}R_{52}$, $COOR_{50}$ and $CONR_{51}R_{52}$;

$R_9$, $R_{29}$, $R_{39}$, $R_{49}$, $R_{59}$, $R_{69}$, $R_{19}$, $R_{79}$, $R_{89}$ and $R_{99}$ are each independently selected from the group consisting of C1-C12 straight or branched alkyl, C2-C12 alkenyl, C3-C12 alkenyl alkyl, with hydrogen atoms on the carbon atoms being unsubstituted or substituted by one or more groups selected from the group consisting of: phenyl, C5-C6 cycloalkyl, C3-C6 heterocyclic group, halogen, $COOR_{20}$, $OR_{20}$, $SR_{20}$, $PO(OC_nH_{2n+1})_2$, and $Si(C_nH_{2n+1})_3$, and wherein n is an integer from 1 to 4;
or $R_9$, $R_{29}$, $R_{39}$, $R_{49}$, $R_{59}$, $R_{69}$, $R_{19}$, $R_{79}$, $R_{89}$ and $R_{99}$ are each independently selected from the group consisting of C3-C12 alkyl and C3-C12 alkenyl alkyl, with its alkyl chain being interrupted by one or more groups selected from the group consisting of O, S, SO, $SO_2$, CO and COO;

or $R_9$, $R_{29}$, $R_{39}$, $R_{49}$, $R_{59}$, $R_{69}$, $R_{19}$, $R_{79}$, $R_{89}$ and $R_{99}$ are each independently selected from the group consisting of C2-C12 alkylene and double bond-containing C4-C12 alkylene, wherein groups connected with the terminal of the C2-C12 alkylene and the double bond-containing C4-C12 alkylene have the same definition as the groups originally connected with $R_9$, $R_{29}$, $R_{39}$, $R_{49}$, $R_{59}$, $R_{69}$, $R_{19}$, $R_{79}$, $R_{89}$ and $R_{99}$;

or $R_9$, $R_{29}$, $R_{39}$, $R_{49}$, $R_{59}$, $R_{69}$, $R_{19}$, $R_{79}$, $R_{89}$ and $R_{99}$ are each independently phenyl unsubstituted or substituted by one or more groups selected from the group consisting of: C1-C8 alkyl, halogen, $OR_{20}$, $SR_{20}$, $COR_{30}$, CN, COOH and

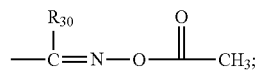

$R_{16}$, $R_{76}$, $R_{86}$, $R_{96}$, $R_{116}$ are each independently selected from the group consisting of C6-C20 aroyl, C4-C10 heteroaryl acyl, $NO_2$, 4,5-diphenylimidazol-2yl; and when $R_{16}$, $R_{76}$, $R_{86}$, $R_{96}$ and $R_{116}$ are each independently selected from the group consisting of C6-C20 aroyl or C4-C10 heteroaryl acyl, substituents at ortho-position of the acyl on the aromatic ring or heteroaromatic ring can be optionally connected with the carbazole ring;

$R_{13}$, $R_{73}$, $R_{83}$, $R_{93}$ and $R_{113}$ are each independently selected from the group consisting of C1-C8 alkyl, and C1-C3 alkyl substituted by C5-C6 cycloalkyl or phenyl at terminal thereof, or the above-mentioned alkyl can optionally form a ring together with carbon or substituents on the carbon on an adjacent parent ring; provided that $R_{16}$, $R_{76}$, $R_{86}$ and $R_{96}$ on the same molecule are each independently selected from C6-C20 aroyl or C4-C20 heteroaroyl group;

or $R_{13}$, $R_{73}$, $R_{83}$ and $R_{93}$ are each independently selected from the group consisting of C6-C20 aryl, C6-C20 aroyl and C4-C20 heteroaroyl, provided that $R_{16}$, $R_{76}$, $R_{86}$ and $R_{96}$ on the same molecule are each independently selected from the group consisting of C6-C20 aroyl, C4-C20 heteroaryl acyl, $NO_2$ and 4,5-diphenylimidazol-2-yl

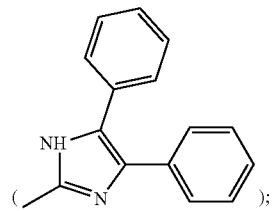 [SMILES: Cc1nc(-c2ccccc2)c(-c2ccccc2)[nH]1]

$R_{10}$, $R_{70}$, $R_{80}$, $R_{90}$, $R_{110}$, $R_{120}$ and $R_{130}$ are each independently selected from C1-C12 alkyl and C6-C20 aryl;
$Ar_1$, $Ar_2$, $Ar_3$, $Ar_4$, $Ar_5$, $Ar_6$, $Ar_7$ and $Ar_8$ are each independently selected from C6-C20 aroyl and C4-C20 heteroaroyl, wherein ortho-position of acyl on $Ar_1$, $Ar_2$ and $Ar_5$ can be optionally connected to a carbazole ring via O atom or S atom;

Y is straight or branched C1-C3 alkylene;
m=0 or 1;
substituents on all the above C6-C20 aryl and C4-C20 heteroaryl comprise H, halogen, CN, $R_{40}$, $OR_{50}$, $SR_{50}$, $NR_{51}R_{52}$, $COOR_{50}$ and $CONR_{51}R_{52}$;
$R_{20}$ and $R_{30}$ are each independently selected from the group consisting of H, C1-C8 alkyl, C1-C8 alkyl substituted by one or more groups selected from halogen and C5-C6 cycloalkyl, phenyl, phenyl substituted by one or more halogen, and C1-C4 alkyl acyl;
$R_{40}$ and $R_{50}$ are each independently selected from the group consisting of C1-C8 alkyl, C1-C8 alkyl substituted by one or more groups selected from F, Cl and hydroxyl, C3-C8 alkyl interrupted by one or more oxygen atoms and substituted by hydroxyl and acetoxy, a five-membered or six-membered ring containing one or two of heteroatoms selected from O, S and N, phenyl, and C1-C4 alkylphenyl;
$R_{51}$ and $R_{52}$ are each independently selected from the group consisting of C1-C4 alkyl, and hydroxyl substituted C1-C4 alkyl;
or $NR_{51}R_{52}$ is a ring structure selected from the group consisting of

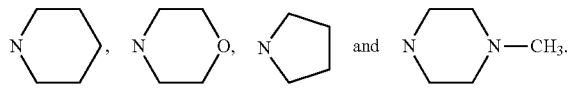

2. The photoinitiator composition of claim 1, wherein the sensitizing agent of formula I is selected from compounds of formulas I-1 to I-36 and any combination thereof:

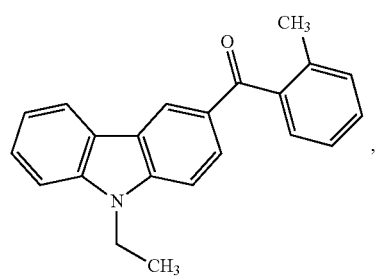
I-1

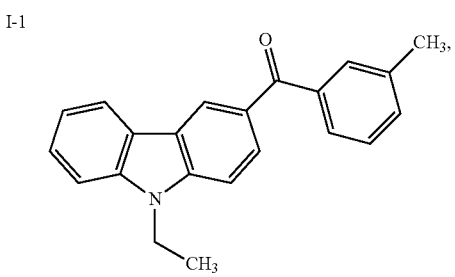
I-2

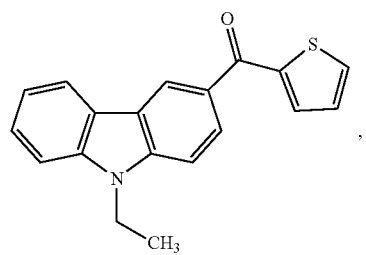
I-3

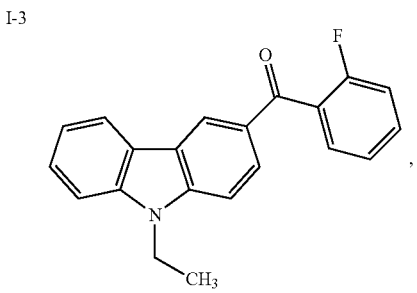
I-4

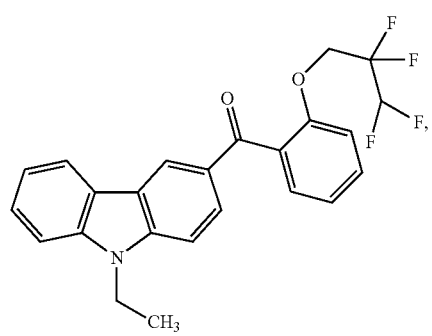
I-5

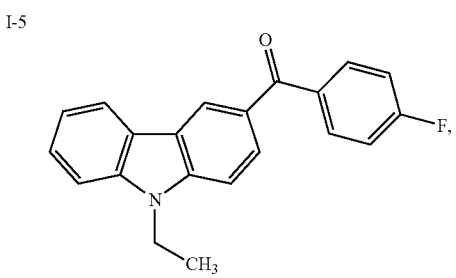
I-6

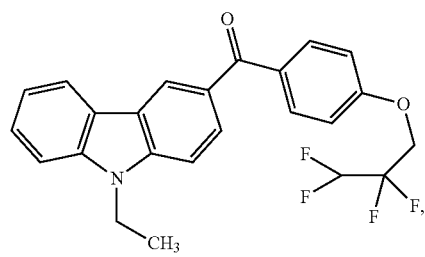
I-7

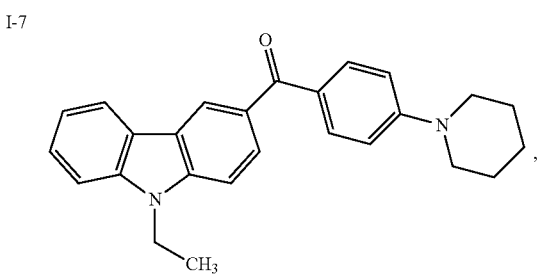
I-8

-continued
I-9
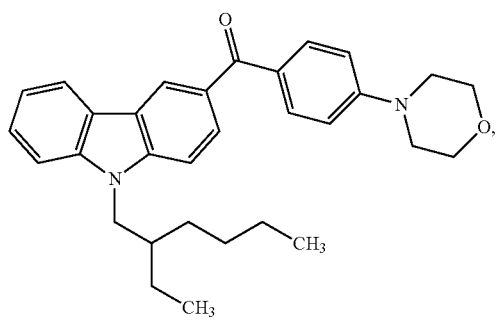
I-10
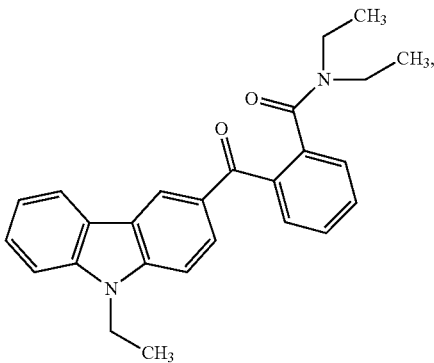
I-11
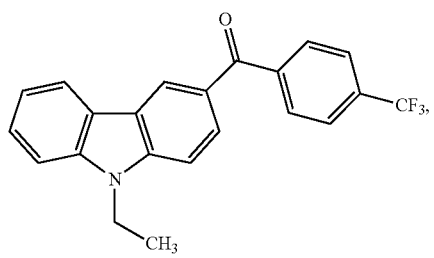
I-12
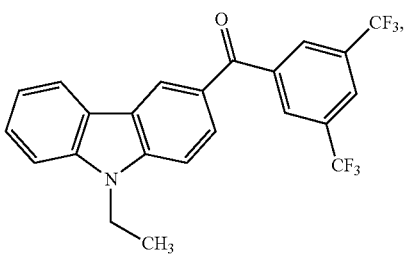
I-13
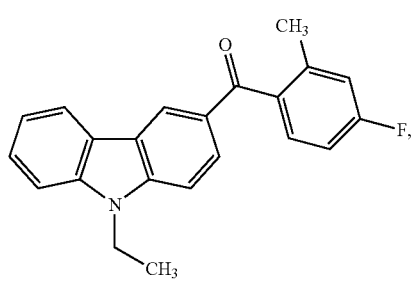
I-14
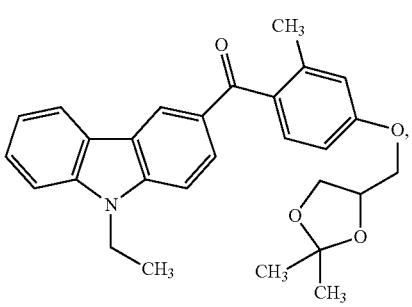
I-15
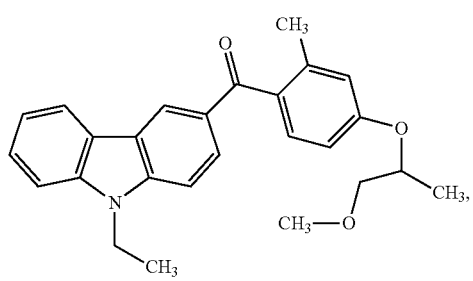
I-16
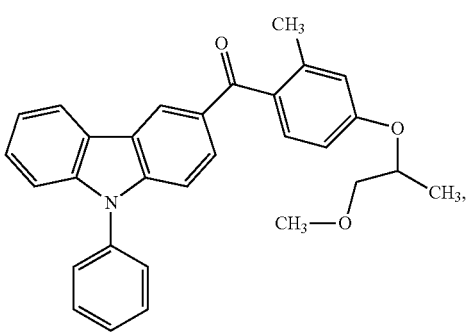
I-17
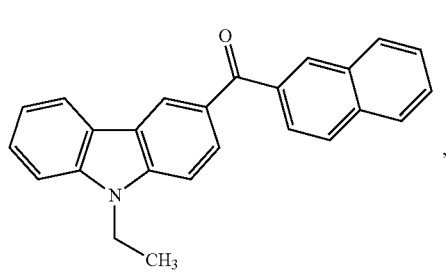
I-18
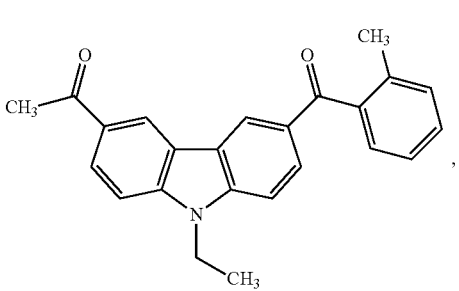

-continued
I-19
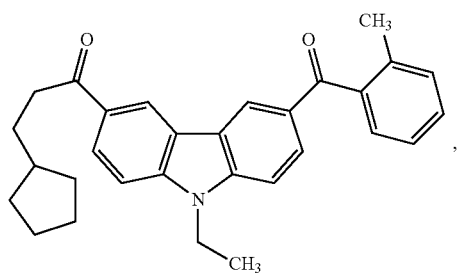
I-20
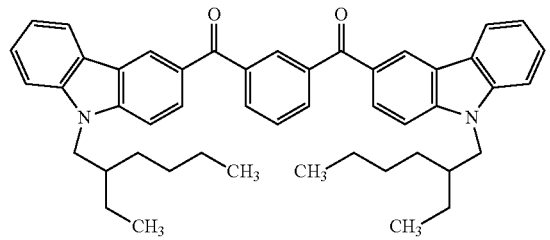
I-21
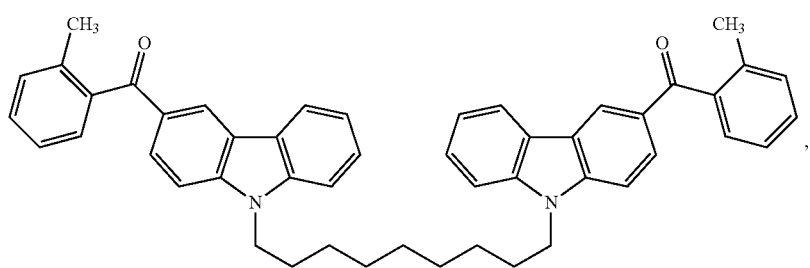
I-22
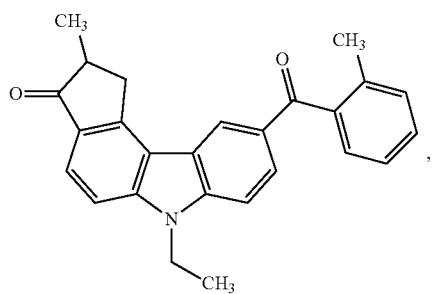
I-23
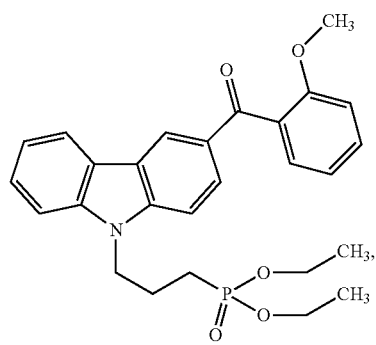
I-24
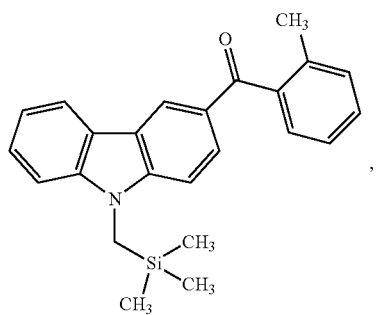
I-25
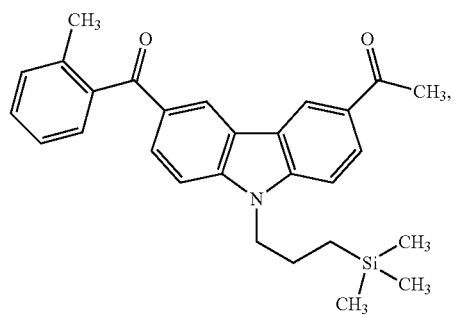
I-26
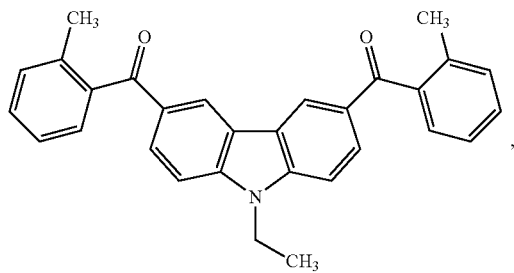
I-27
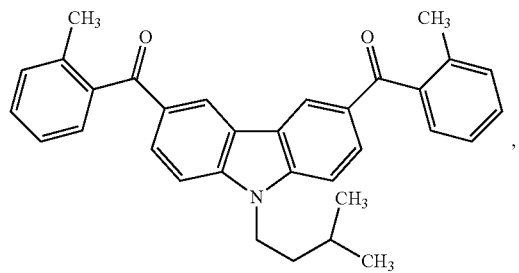

-continued
I-28
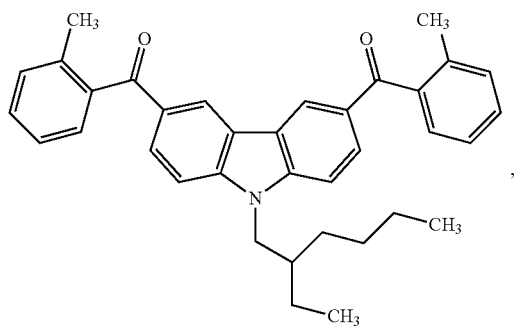
I-29
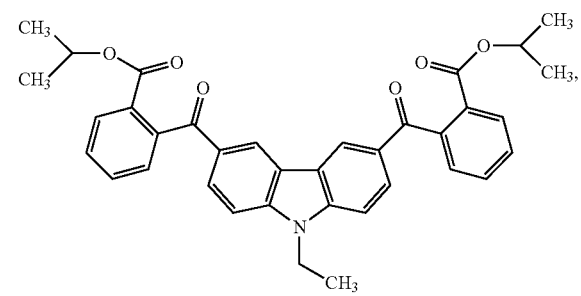
I-30
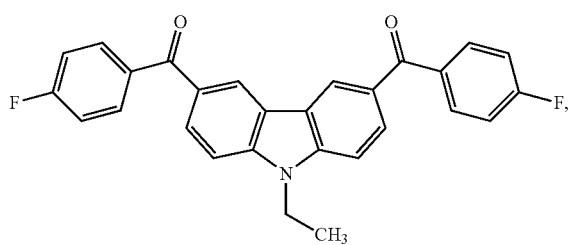
I-31
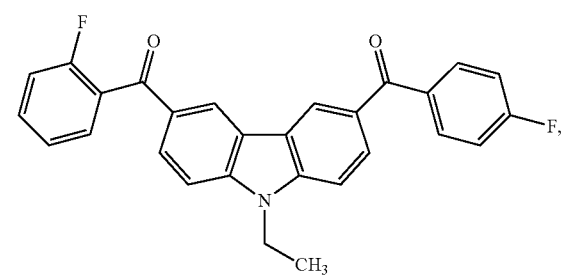
I-32
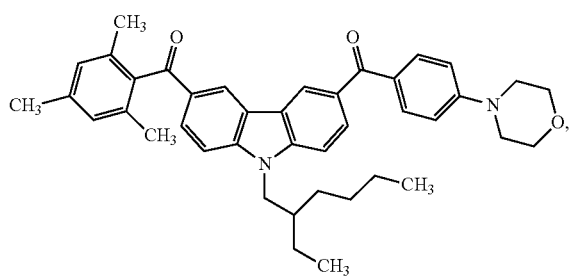
I-33
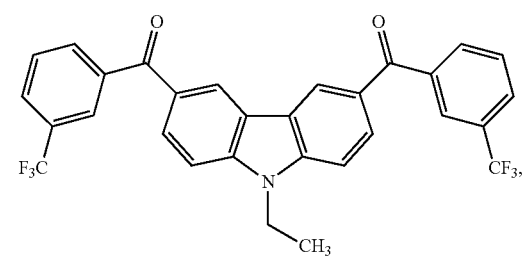
I-34
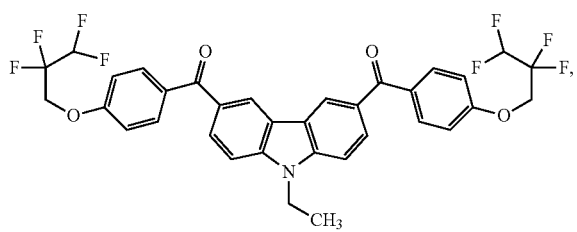
I-35
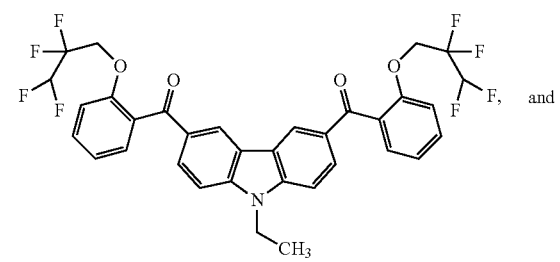
and
I-36
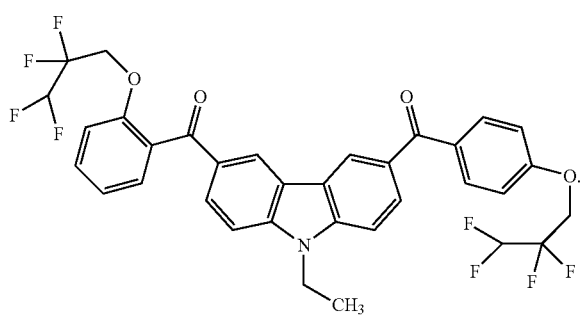

3. The photoinitiator composition of claim 1, wherein the sensitizing agent of formulas II-A to II-H is selected from compounds of formulas II-1 to II-16 and any combination thereof:
II-1
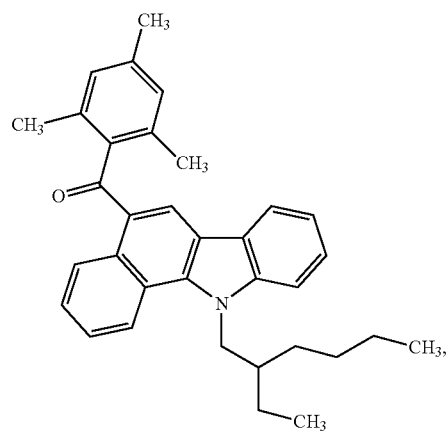
II-2
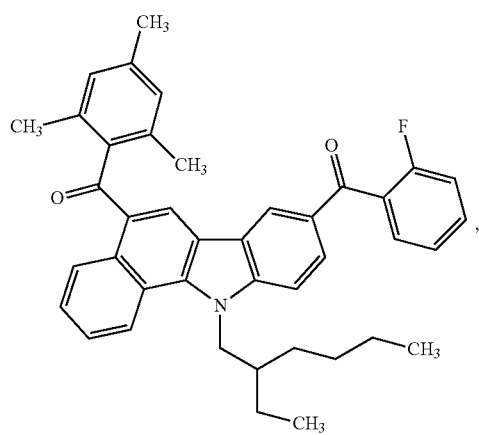
II-3
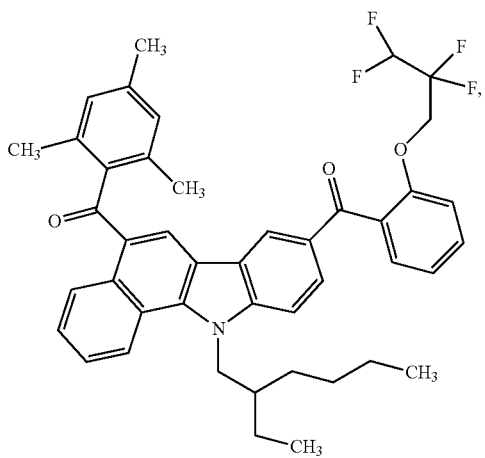
-continued
II-4
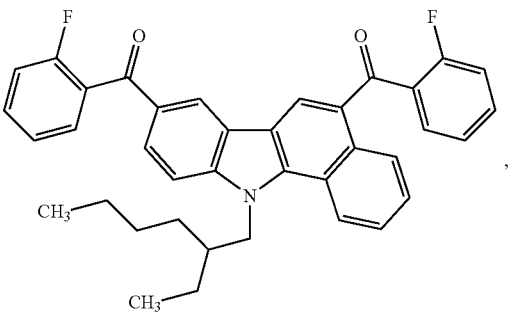
II-5
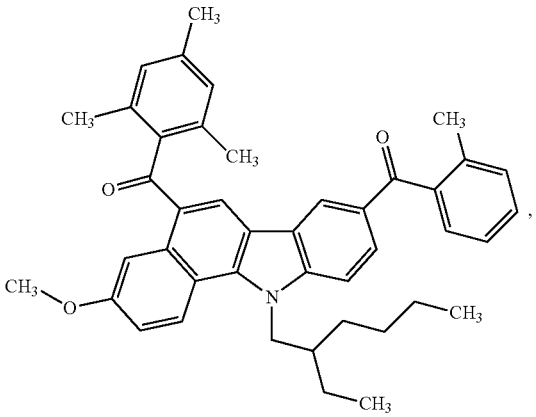
II-6
II-7
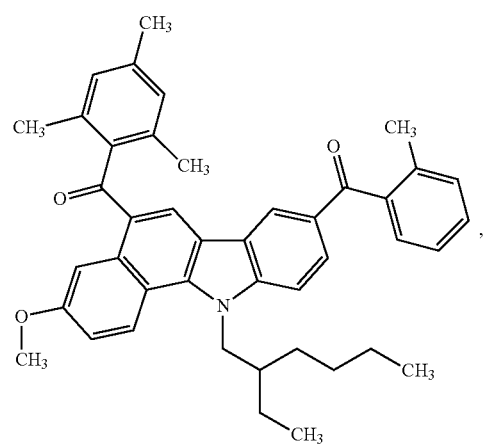

-continued
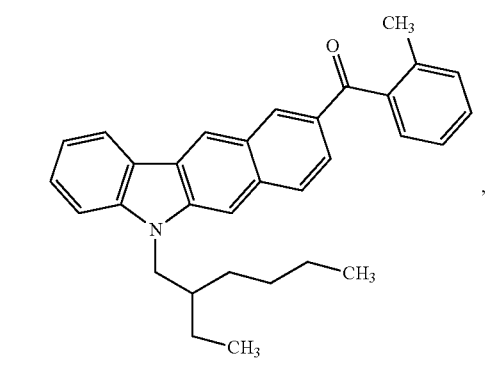
II-8
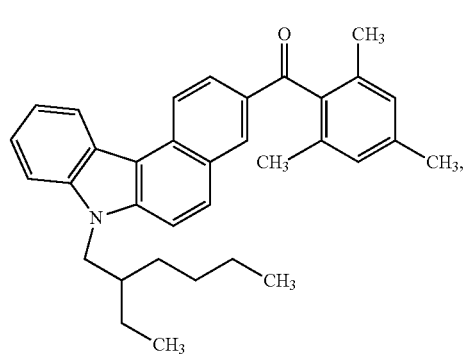
II-9
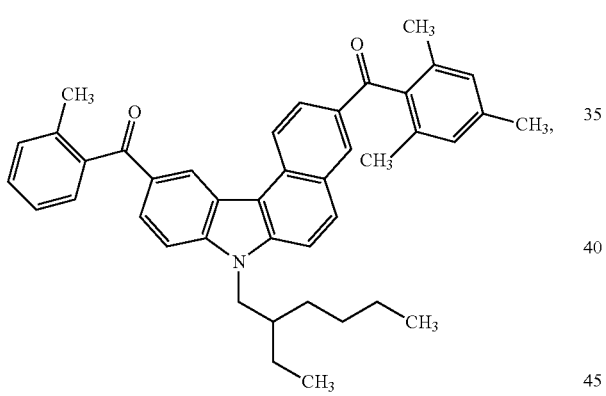
II-10
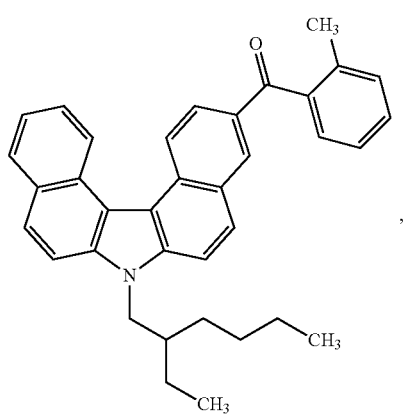
II-11
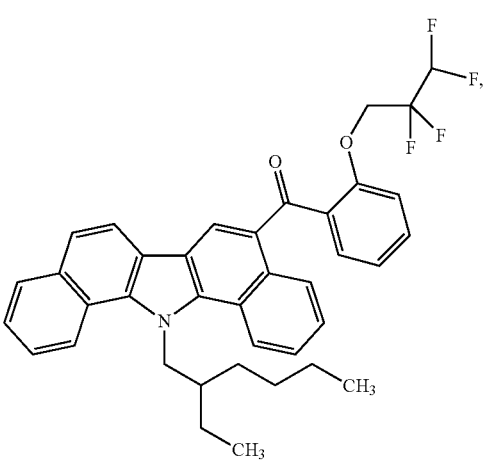
II-12
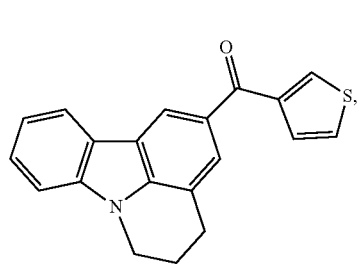
II-13
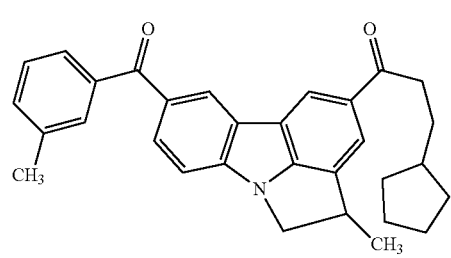
II-14
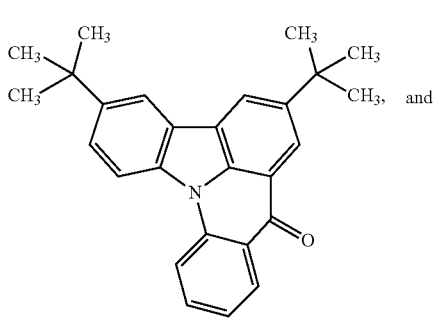
II-15, and II-16
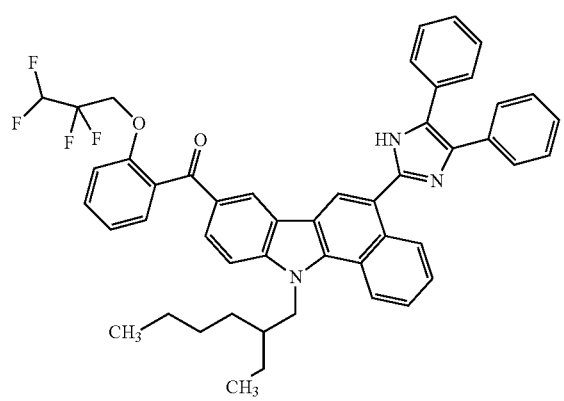
4. The photoinitiator composition of claim 1, wherein the carbazolyl oxime ester of formula III is selected from compounds of formulas III-1 to III-16 and any combination thereof:
III-1
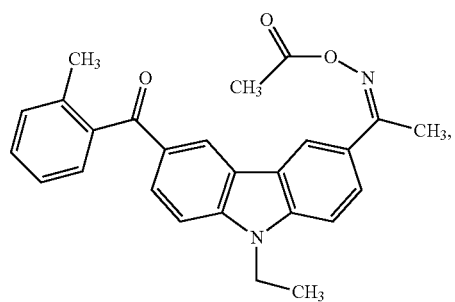
III-2
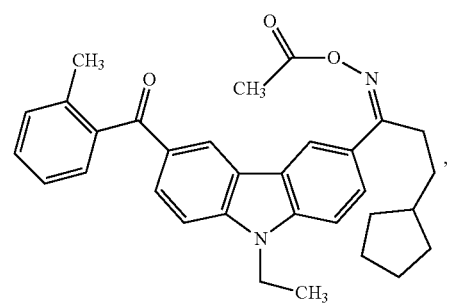
III-3
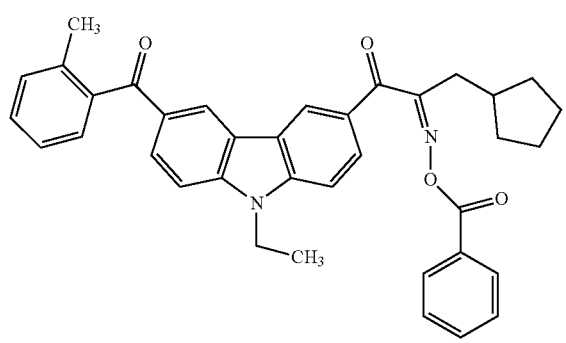
III-4
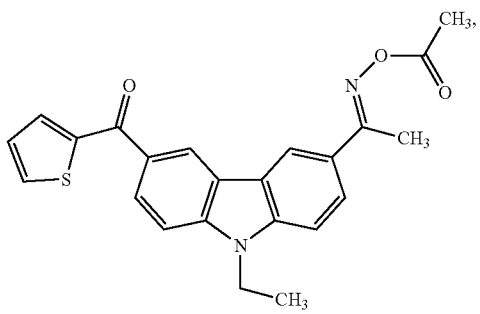
III-5
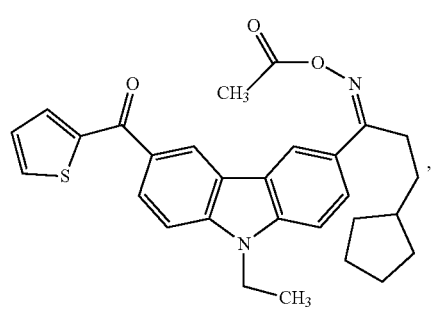
III-6
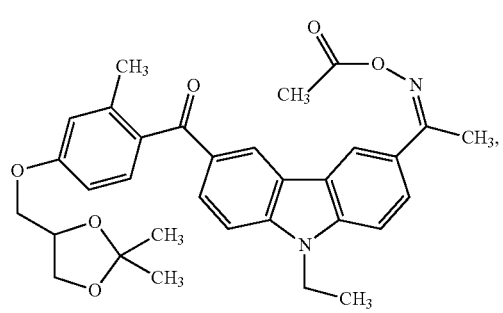
III-7
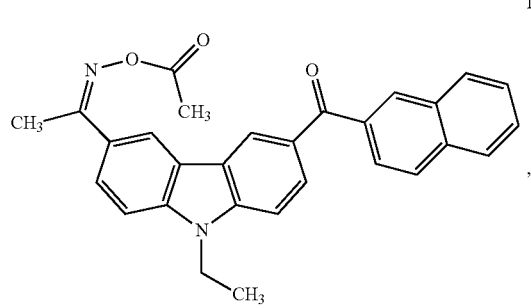
III-8
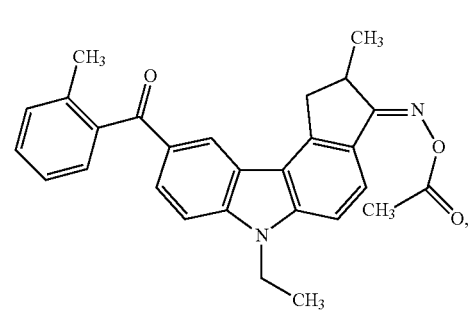

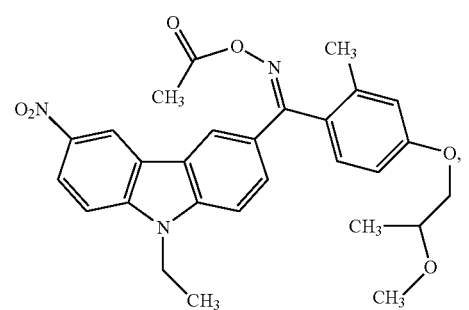
III-9
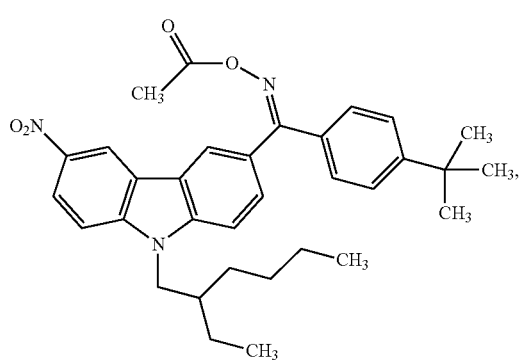
III-10
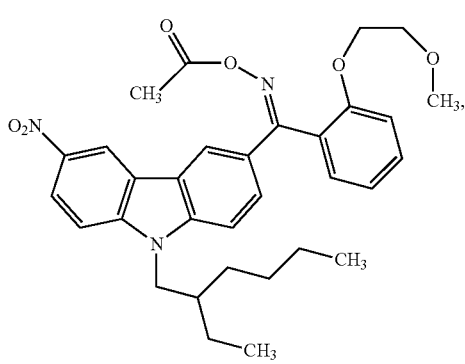
III-11
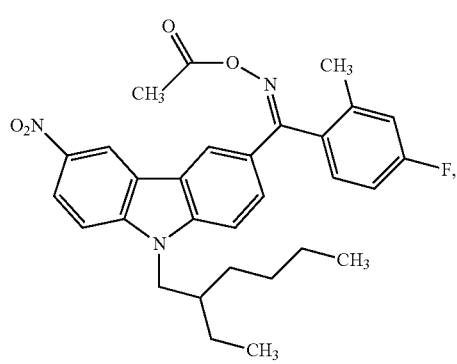
III-12
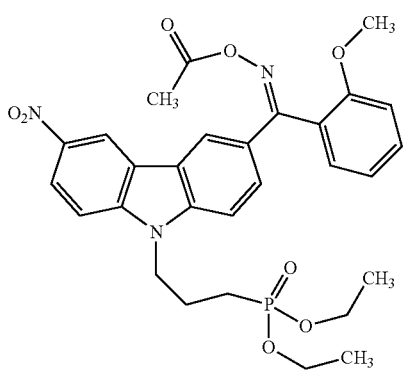
III-13
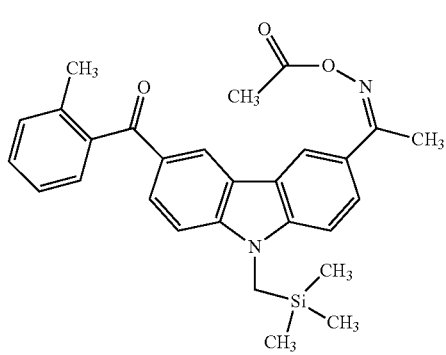
III-14
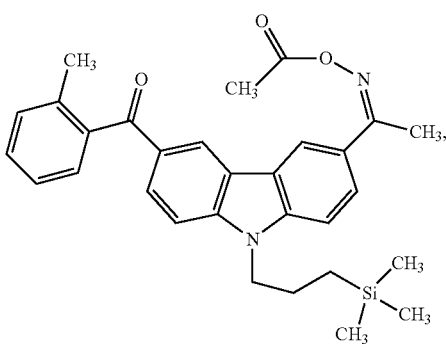
III-15
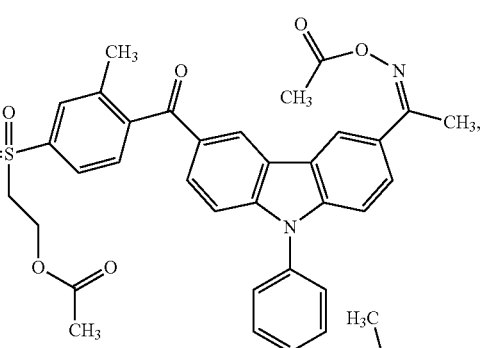
III-16
and III-17
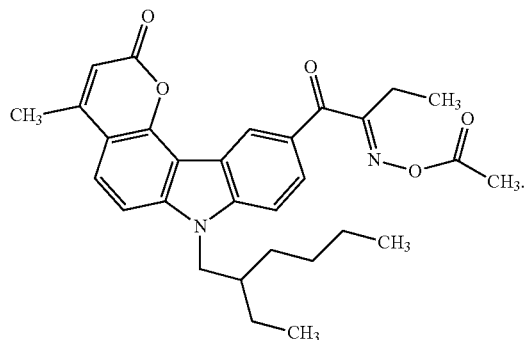
IV-3
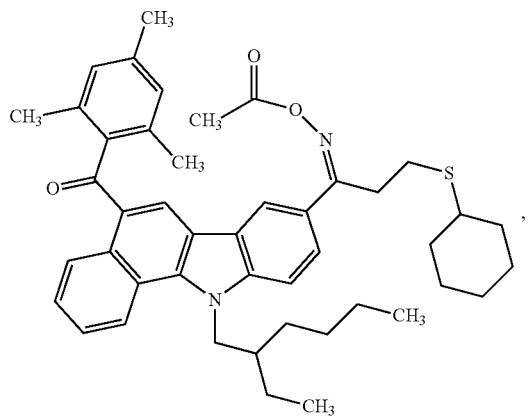
5. The photoinitiator composition of claim 1, wherein the carbazolyl oxime ester of formulas IV-A to IV-E is selected from compounds of formulas IV-1 to IV-21 and any combination thereof:
IV-1
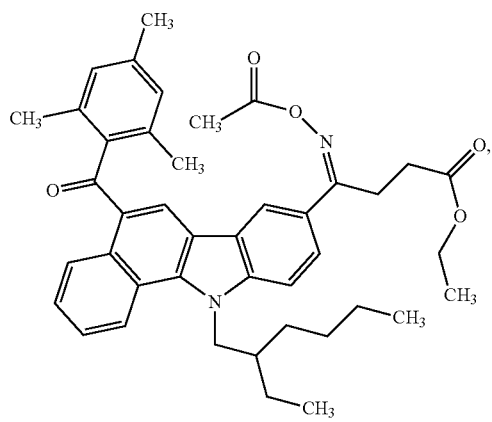
IV-4
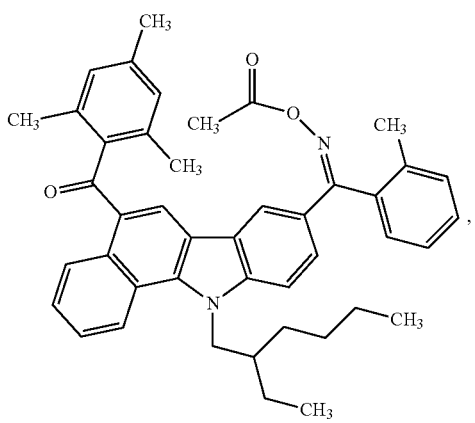
IV-2
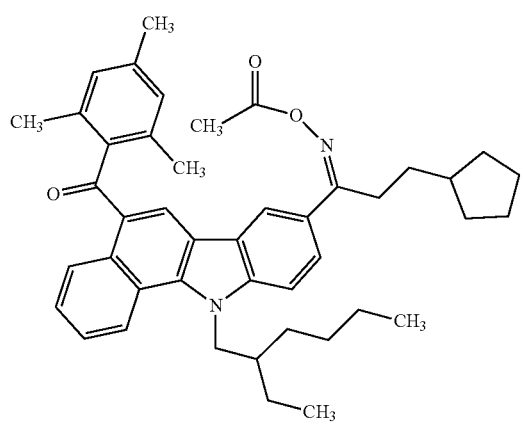
IV-5
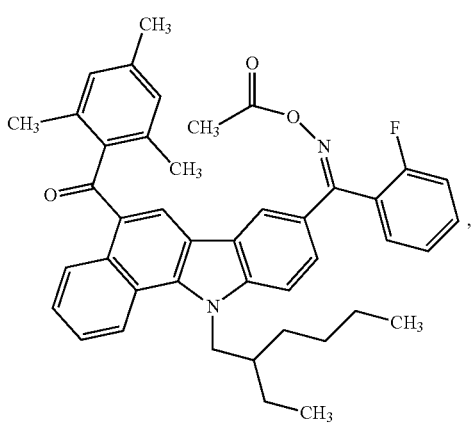

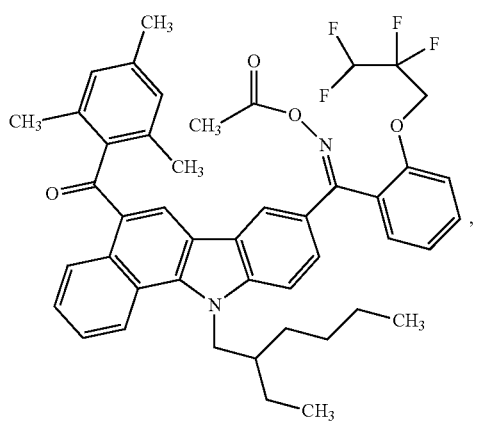
IV-6
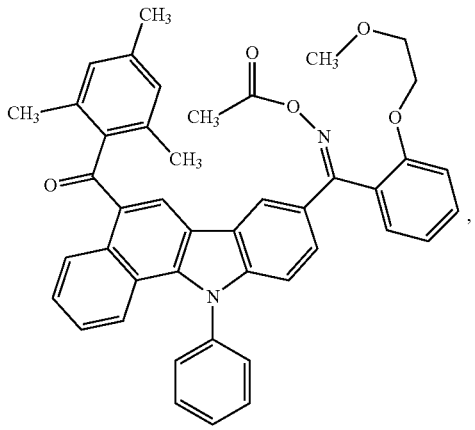
IV-9
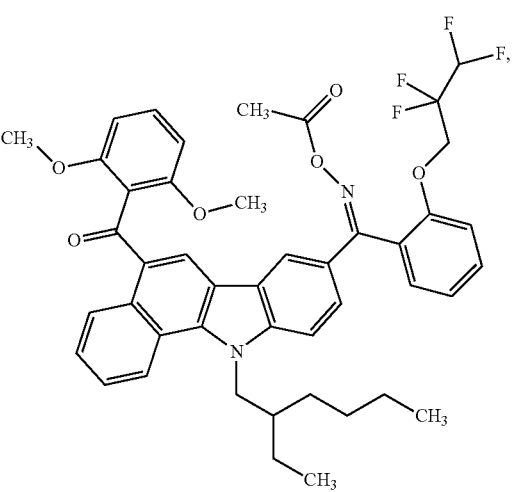
IV-10
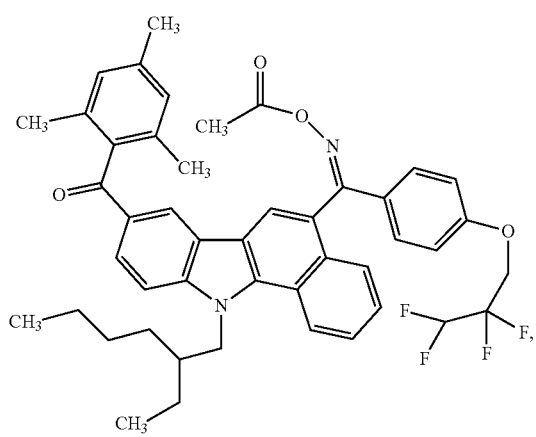
IV-7
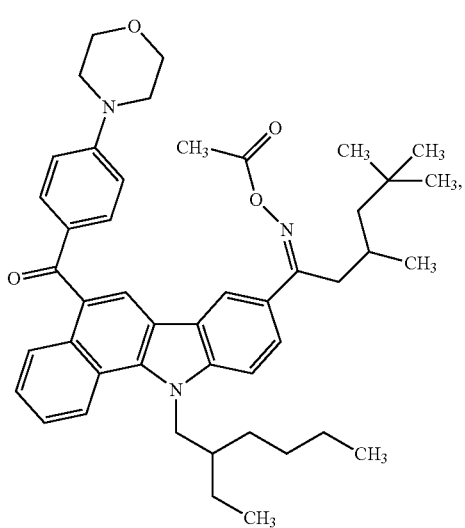
IV-11
IV-8

IV-12
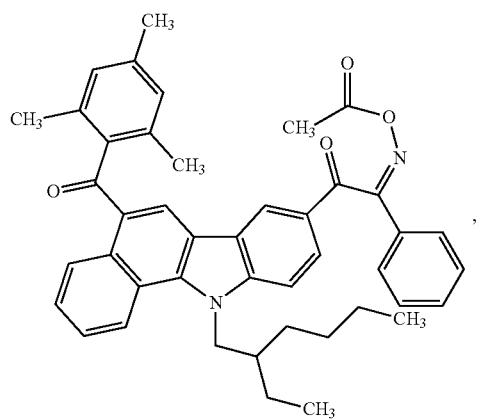
IV-13
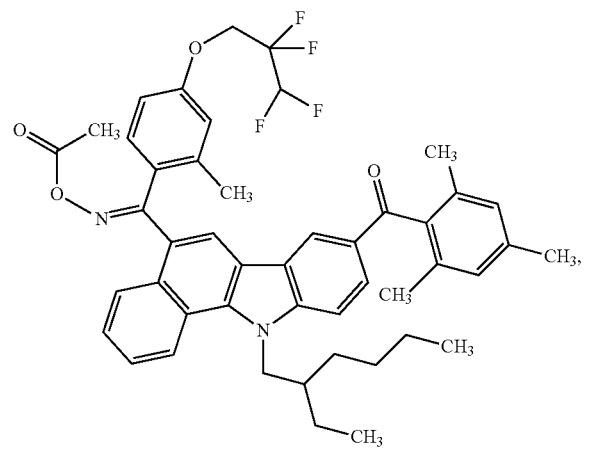
IV-14
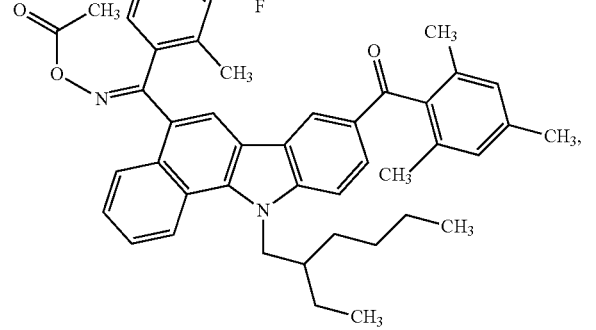
IV-15
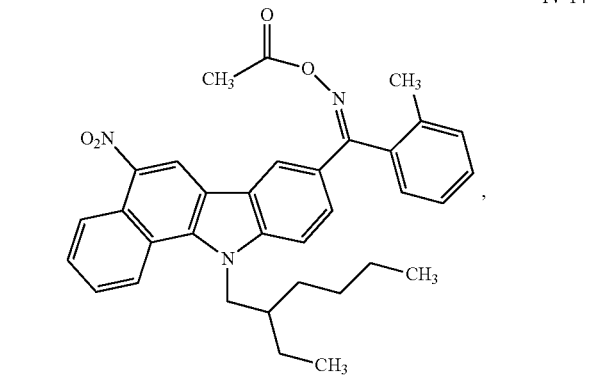
IV-16
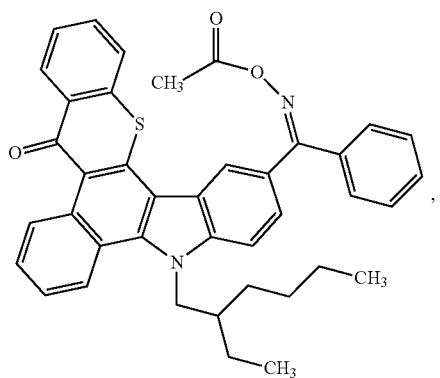
IV-17
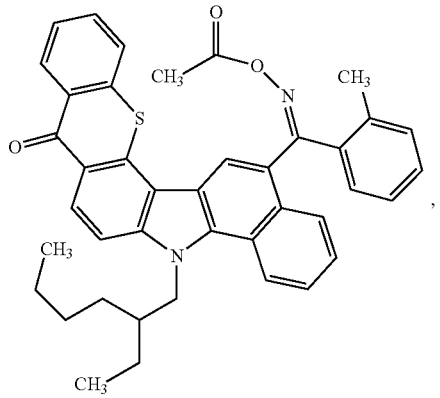
IV-18
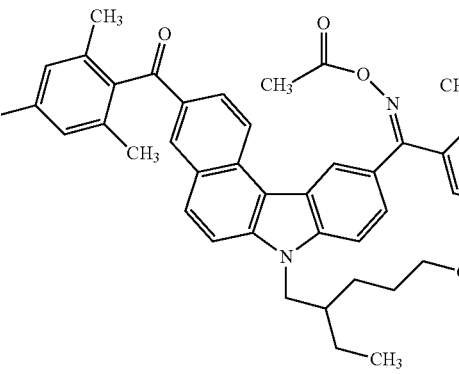
IV-19
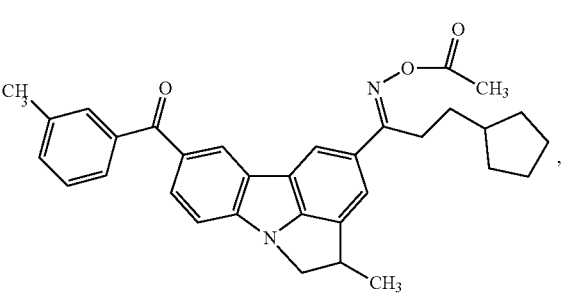

-continued

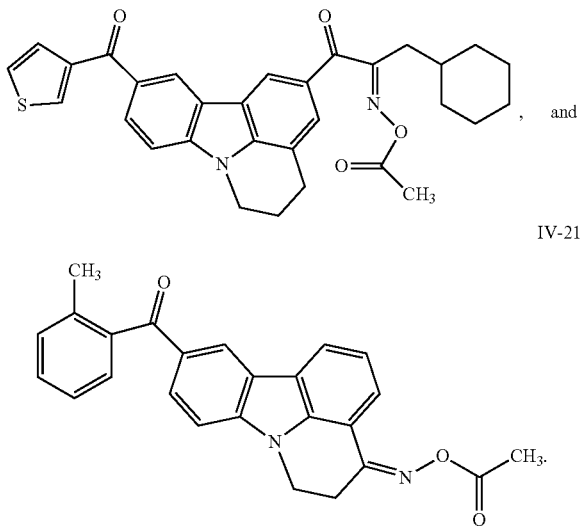

6. The photoinitiator composition of claim 1, wherein a molar ratio of the sensitizing agent to the carbazolyl oxime ester is 0.1:1 to 1.4:1.

7. A photocurable composition, comprising:
a. at least one photoinitiator composition of claim 1, and
b. at least one radically polymerizable compound.

8. The photocurable composition of claim 7, wherein the radically polymerizable compound is selected from the group consisting of an acrylate compound, a methacrylate compound, a resin containing acrylate or methacrylate groups, and any mixtures thereof.

9. The photocurable composition of claim 7, wherein component a accounts for 0.2-10% by weight of a total weight of all solid components.

10. An ink comprising the photocurable composition of claim 7.

11. A coating comprising the photocurable composition of claim 7.

12. An adhesive comprising the photocurable composition of claim 7.

13. A photoresist, comprising the following components:
a. at least one photoinitiator composition of claim 1,
b. a multifunctional acrylate monomer,
c. an alkali-soluble resin,
d. a pigment, and
e. a solvent.

14. A black photoresist, the photoresist of claim 13, wherein the pigment is well dispersed carbon black or titanium black.

15. A black matrix prepared from the black photoresist of claim 14.

16. An optical spacer prepared from the black photoresist of claim 14.

17. A color filter device prepared by a filter processing process using the photoresist of claim 13 as a raw material.

18. The photoinitiator composition of claim 6, wherein the molar ratio of the sensitizing agent to the carbazolyl oxime ester is 0.22:1 to 1.3:1.

19. The photocurable composition of claim 9, wherein component a accounts for 1-8% by weight of a total weight of all solid components.

* * * * *